(12) United States Patent
McPhillips et al.

(10) Patent No.: US 7,648,696 B2
(45) Date of Patent: *Jan. 19, 2010

(54) COMPOSITION FOR INHALATION COMPRISING DELTA-9-TETRAHYDROCANNABINOL IN A SEMIAQUEOUS SOLVENT

(75) Inventors: Andrea M McPhillips, Columbus, OH (US); Julia J Economou, Hilliard, OH (US); Mahendra G Dedhiya, Doublin, OH (US); Beverly Ann Wynne, Worthington, OH (US)

(73) Assignee: Unimed Pharmaceuticals, LLC, Marietta, GA (US)

( * ) Notice: Subject to any disclaimer, the term of this patent is extended or adjusted under 35 U.S.C. 154(b) by 309 days.

This patent is subject to a terminal disclaimer.

(21) Appl. No.: 10/656,304

(22) Filed: Sep. 5, 2003

(65) Prior Publication Data

US 2004/0162336 A1    Aug. 19, 2004

Related U.S. Application Data

(63) Continuation-in-part of application No. 09/639,289, filed on Aug. 15, 2000, now Pat. No. 6,747,058.

(60) Provisional application No. 60/150,023, filed on Aug. 20, 1999.

(51) Int. Cl.
*A01N 25/02* (2006.01)
*A61K 31/35* (2006.01)

(52) U.S. Cl. .................................. 424/43; 514/454
(58) Field of Classification Search ................ 424/43; 514/454

See application file for complete search history.

(56) References Cited

U.S. PATENT DOCUMENTS

| | | | |
|---|---|---|---|
| 4,635,651 A | 1/1987 | Jacobs | |
| 4,933,363 A | 6/1990 | ElSohly | |
| 5,258,336 A | 11/1993 | LaMastro et al. | |
| 5,447,729 A | 9/1995 | Belenduik et al. | |
| 5,492,688 A | 2/1996 | Byron et al. | |
| 5,502,076 A | 3/1996 | Dixit et al. | |
| 5,508,023 A | 4/1996 | Byron et al. | |
| 5,508,037 A | 4/1996 | ElSohly | |
| 5,540,934 A | 7/1996 | Touitou | |
| 5,635,530 A | 6/1997 | Mechoulam et al. | |
| 5,716,638 A | 2/1998 | Touitou | |
| 5,736,124 A | 4/1998 | Akehurst et al. | |
| 5,804,592 A | 9/1998 | Volicer | |
| 5,847,128 A | 12/1998 | Martin et al. | |
| 5,874,443 A | 2/1999 | Kiely et al. | |
| 5,916,540 A | 6/1999 | Akehurst et al. | |
| 5,922,306 A | 7/1999 | Akehurst et al. | |
| 5,939,429 A | 8/1999 | Kunos et al. | |
| 6,162,829 A | 12/2000 | Burstein | |
| 6,294,192 B1 | 9/2001 | Patel et al. | |
| 6,509,005 B1 * | 1/2003 | Peart et al. | ..................... 424/45 |

FOREIGN PATENT DOCUMENTS

| | | |
|---|---|---|
| WO | WO 98/29096 | 7/1998 |
| WO | WO 99/32107 | 7/1999 |
| WO | WO 00/24362 | 5/2000 |
| WO | WO 00/27359 | 5/2000 |
| WO | WO 01/13886 | 3/2001 |

OTHER PUBLICATIONS

Williams, et al., "Bronchodilator Effect of Delta-Tetrahydrocannabinol Administered By Aerosol to Asthmatic Patients," Thorax, vol. 31 (No. 6), p. 720-723, (1976).
Lichtman, et al., "Pharmacological Evaluation of Aerosolized Cannabinoids in Mice," European Journal of Pharmacology, vol. 399 (No. 2-3), p. 141-149, (2000).
Ault, "Techniques and Experiments for Organic Chemistry," Waveland Press, Inc. (Prospect Heights, Illinois), p. 44-50, 183-194, (1987).
Dedhiya, et al., "Current Concepts for Delivery of D-9 THC: Prospects For Cannabinoid Drug Development," (1998).
Vachon, et al., "Airways Response to Aerosolized Delta-9-Tetrahydrocannabinol: Preliminary Report," The Therapeutic Potential of Marihuana, Plenum Medical Book Company (New York and London), p. 111-121, (1976).
Fratello, "NIH Study Helps the Case For Medical Marijuana," The Sacremento Bee, (Sep. 5, 1997).
Lewis, "Just Say 'Research'," The Scientist, vol. 12 (No. 3), p. 1&6, (Feb. 2, 1998).
"Aerosol Delivery: Stability Data" (Feb. 18, 1998).
Little, "Studies of Stability and Purification of Delta 9-Tetrahydrocannabinol," (Nov. 1970).
Garrett, et al., "Physicochemical Properties, Solubility, and protein Binding of Delta 9-Tetrahydrocannabinol," Journal of Pharmaceuticall Sciences, p. 1056-1064, (1974).
Ohlsson, et al., "Plasma Delta-9-Tetrahydrocannabinol Concentrations and Clinical Effects After Oral and Intravenous Administration and Smoking," Clinical Pharmacology and Therapeutics, vol. 28 (No. 3), p. 409-416, (Sep. 1980).

(Continued)

*Primary Examiner*—Sreeni Padmanabhan
*Assistant Examiner*—Renee Claytor
(74) *Attorney, Agent, or Firm*—Mayer Brown LLP

(57) ABSTRACT

A stable composition for rapid delivery by inhalation to the lungs, and subsequently to the bloodstream, is provided. The composition comprises a therapeutically effective amount of delta-9-tetrahydrocannabinol in a pharmaceutically-acceptable semiaqueous solvent comprising an alcohol, water and a glycol. A composition comprising volumetric ratios of ethanol:water:propylene glycol selected from those in the range of from 10-70:10-30:20-80, respectively, having a combined total of 100 is also provided. A sterile and/or preserved sealed unit-or multi-unit dosage form of delta-9-tetrahydrocannabinol is further provided.

10 Claims, 36 Drawing Sheets

OTHER PUBLICATIONS

Perez-Reyes, et al., "Pharmacology of Orally Administered Delta-9-Tetrahydrocannabinol," Clinical Pharmacology and Therapeutics, vol. 14 (No. 1), p. 48-55, (1973).

Tashkin, et al., "Bronchial Effects of Aerosolized Dleta-9-Tetrahydrocannabinol in Healthy and Asthmatic Subjects," American Review of Respiratory Disease, p. 57-65, (1977).

Vachon, L. et al, Airways Response to Aerosolized Delta-9-Tetrahydro-Cannabinol: Prliminary Report, The Therapeutic Potential of Marihuana, 1976, Chapter 8, 111-121, Plenum Medical Book Company, New York, US.

Williams, S.J. et al, Bronchodilator effect of delta-tetrahydrocannabinol administered by aerosol to asthmatic patients, Thorax, 1976, 720-723, vol. 31, No. 6.

Lichtman, A. et al, Pharmacological Evaluation of Aerosolized Cannabinoids in Mice, European Journal of Phamacology, 2000, 141-149, vol. 399, No. 2-3.

* cited by examiner

US 7,648,696 B2

COMPOSITION FOR INHALATION COMPRISING DELTA-9-TETRAHYDROCANNABINOL IN A SEMIAQUEOUS SOLVENT

This application is a continuation-in-part of U.S. patent application Ser. No. 09/639,289, filed Aug. 15, 2000, which is a non-provisional of U.S. Provisional Application No. 60/150,023, filed Aug. 20, 1999. This application claims priority to all such previous applications, and such applications are hereby incorporated herein by reference.

FIELD OF THE INVENTION

The present invention relates to a fast-acting delivery system for delta-9-tetrahydrocannabinol (dronabinol) to improve bioavailability. More particularly, it provides a stable composition for delivery by inhalation to the lungs, and subsequently to the bloodstream, the composition comprising a therapeutically effective amount of delta-9-tetrahydrocannabinol (also known as "delta-9-THC") and a pharmaceutically-acceptable semiaqueous solvent.

BACKGROUND OF THE INVENTION

Dronabinol, a synthetic version of delta-9-tetrahydrocannabinol (delta-9-THC), is currently approved by regulatory authorities for use as an antiemetic in cancer chemotherapy as well as an appetite stimulant for patients afflicted with the AIDS virus. The product is currently marketed under the commercial name Marinol® as an oral soft gelatin capsule in which the drug substance is dissolved in sesame oil.

Dronabinol is the principal psychoactive agent in marijuana and has a number of complex effects on the central nervous system, including central sympathomimetic activity. Dronabinol also has anti-nausea/antiemetic activity. The mechanism whereby dronabinol acts to reduce nausea and emesis is not well understood, in part because the neuropharmacology of the vomiting center and its connections to input centers is not known in sufficient detail. Dronabinol, however, appears to act via a mechanism distinct from that of other antiemetics which function, typically, by dopaminergic antagonism, such as, phenothiazines, butyrophenones, or benzamides or that of H, antagonists, which are used most commonly for prevention of motion sickness and are included in many antiemetic regimens to suppress the extrapyramidal effects of the neuroleptic anti-dopaminergics.

Bioavailability of the current formulation ranges from 10-20% due to a high first pass metabolism associated with oral administration. The current formulation has an onset of action ranging from 0.5 to 1 hour. In addition, maximum concentrations may not be reached until several hours after oral administration.

As discussed, dronabinol is almost completely absorbed (90-95%) after single oral doses. Dronabinol has an extensive first pass hepatic metabolism and, also, high lipid solubility. As a result, only 10% to 20% of an orally administered dose will be found in systemic circulation at peak levels, the balance being sequestered in lipid tissues or having been metabolized during the first pass. Dronabinol and its principle active metabolite, 11-OH-delta-9-THC, are present in approximately equal concentrations in plasma. Concentration of both the parent drug and the metabolite peaks at approximately 2 to 4 hours after oral dosing and declines over several days. Values for clearance average are about 0.2 L/kg/hr, but are highly variable due to the complexity of cannabinoid distribution.

The elimination phase of dronabinol can be described using a two-compartment model with an initial alpha half-life of about 4 hours and a terminal beta half-life of 25 to 36 hours.

Because of its very high lipid solubility, dronabinol is sequestered in fatty tissues leading to a very large apparent volume of distribution, approximately 10 L/kg and to the creation of a depot compartment from which dronabinol is excreted at low levels for prolonged periods of time. This depot compartment produces the long beta half-life excretion phase for dronabinol. Biliary excretion is the major route of elimination with about half of the oral dose being recovered from the feces within 72 hours as contrasted with 10% to 15% recovered from urine.

The major urinary metabolite in humans following oral administration is 11-nor-9-lc carboxy-delta-9-tetrahydrocannabinol. It accounts for approximately 27% of the total THC metabolites excreted in urine. Less than 5% of an oral dose is recovered unchanged in the feces.

It would be desirable to improve bioavailbity and quicken onset of action for the above indications as well as for the treatment of alternative conditions, such as spinal cord spasticity, glaucoma, and Alzheimer's disease. Alternative routes previously suggested to overcome oral delivery limitations include the administration of drugs (including delta-9-tetrahydrocannabinol) through inhalation. It has been demonstrated in the literature, for example, that smoking marijuana cigarettes (the main constituent being dronanbinol, i.e., delta-9-THC) results in improved bioavailability (60-70%). However, there are obvious disadvantages relating to smoking marijuana, including raw material impurities, depression of alveolar macrophage activity, and bronchial irritation. Another approach suggested in initial reports at a meeting on Feb. 24, 1998, sponsored by the Institute of Medicine, National Academy of Sciences, Division of Neuroscience and Behavioral Health in Washington, D.C., was to study and use particle size data developed in a conventional nebulizer system to try to enhance bioavailability of delta-9-tetrahydrocannabinol after deep lung administration. Among the suggested routes of administration suggested by the prior art are those using aerosol formulations to be inhaled as described in Volicer, U.S. Pat. No. 5,804,592, granted Sep. 8, 1998, based on Provisional Application with a priority date of May 7, 1997. However, as presently advised, there has been no prior disclosure of experiments which used formulations comprising delta-9-tetrahydrocannabinol and semiaqueous solvents comprising judiciously selected volumetric ratios of alcohol, water and pharmaceutically acceptable glycols to enhance partitioning, and no evidence of enhanced bioavailability in warm-blooded animals, including humans, has been known for such compositions prior to the present invention. It still remains desirable, therefore, to develop a new safe, fast acting delivery system for delta-9-tetrahydrocannabinol to improve bioavailability, and such a system is the subject matter of the present invention.

SUMMARY OF THE INVENTION

In accordance with the present invention there are provided stable compositions for rapid delivery by inhalation to the lungs, and subsequently to the bloodstream, the compositions comprising a therapeutically effective amount of delta-9-tetrahydrocannabinol in a pharmaceutically-acceptable semiaqueous solvent comprising an alcohol, water and a glycol, in relative volumetric amounts sufficient:

(i) to aerosolize the composition to a mean mass median aerodynamic diameter in the range of from about 1 up to about 10 μM; and (ii) to enhance partitioning by producing a stable clear solution near the solubility point of the delta-9-tetrahydrocannabinol.

Among the preferred features of the invention are such compositions wherein: the delta-9-tetrahydrocannabinol comprises from about 0.1 to about 200 mg/mL, and especially 25 and 50 mg/mL; the solvent comprises ethanol, water and propylene glycol; the volumetric ratios of ethanol:water:propylene glycol are selected from those in the range of from about: 10-70:10-30:20-80, respectively, having a combined total of 100; the volumetric ratios of ethanol:water:propylene glycol are selected from those in the range of from 10-70:10:20-80, respectively, having a combined total of 100; the volumetric ratios of ethanol:water:propylene glycol are 35:10:55, respectively, having a combined total of 100.

Also contemplated by the present invention are sterile or preserved sealed single-unit and/or multi-unit dosage forms of delta-9-tetrahydrocannabinol comprising a container and a stable composition for rapid delivery by inhalation to the lungs and subsequently to the bloodstream, as first defined above, and especially those wherein the container comprises Type I Amber Glass with a suitable liner.

DETAILED DESCRIPTION OF THE INVENTION

Figure 1A:
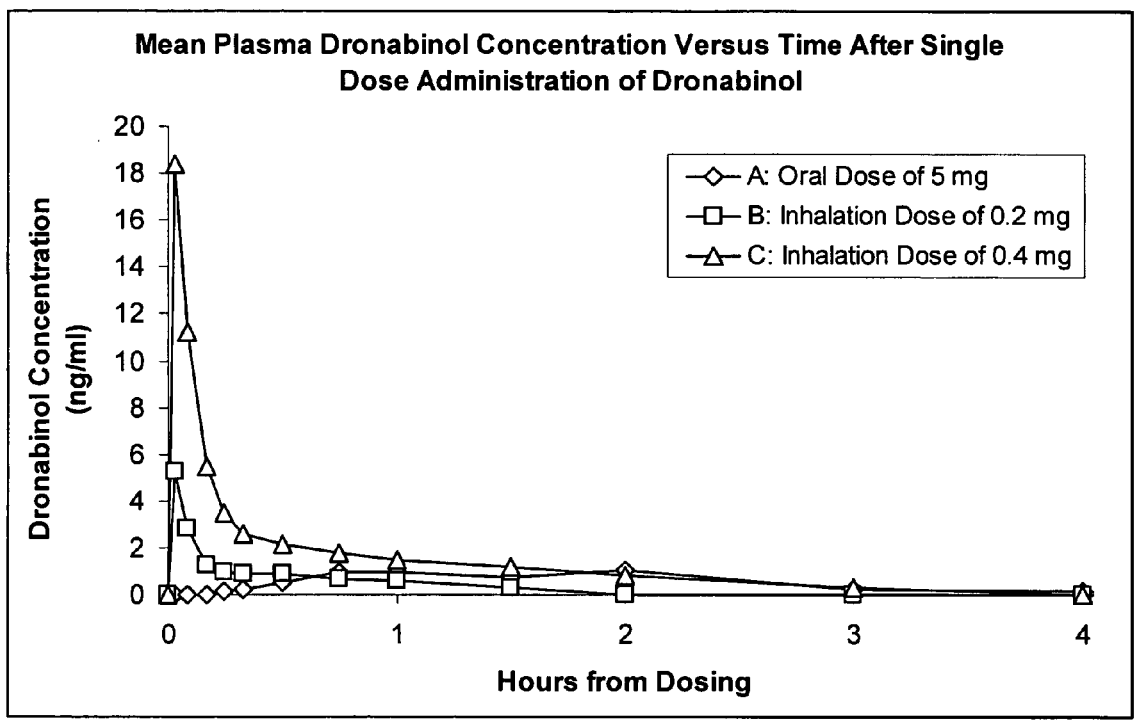
FIGS. 1A and 1B are graphs showing mean dronabinol plasma concentration versus time for treatments A-C (FIG. 1A) and D-G (FIG. 1B), after single dose administration.
Figure 1B:
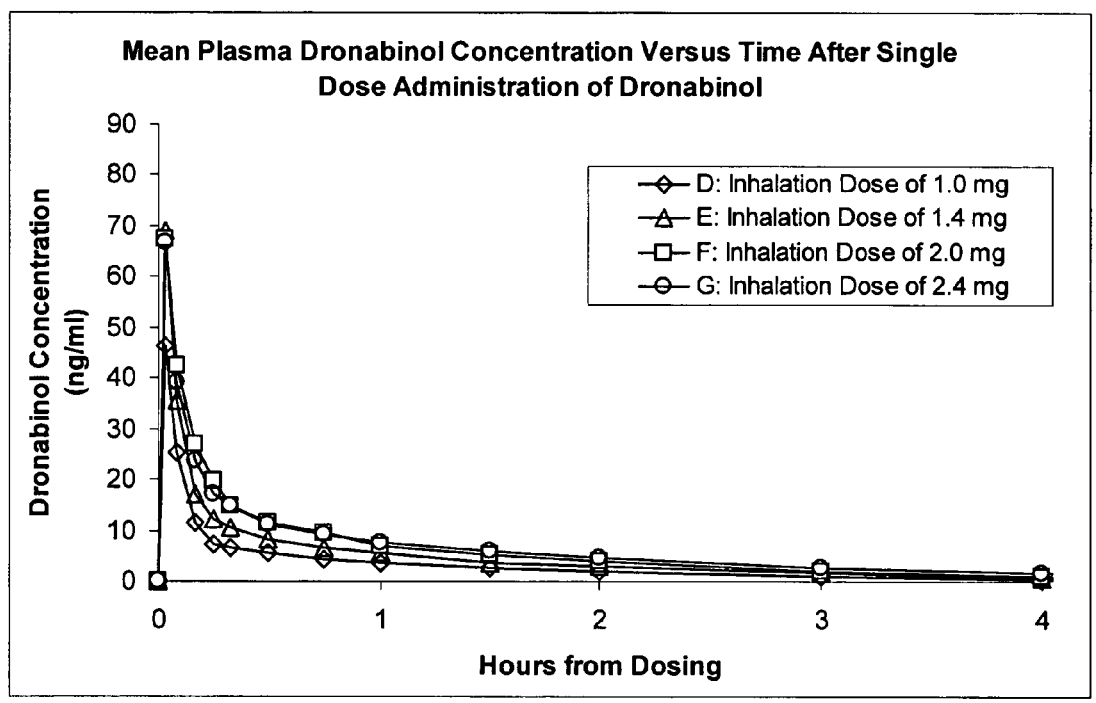
Figure 1C:
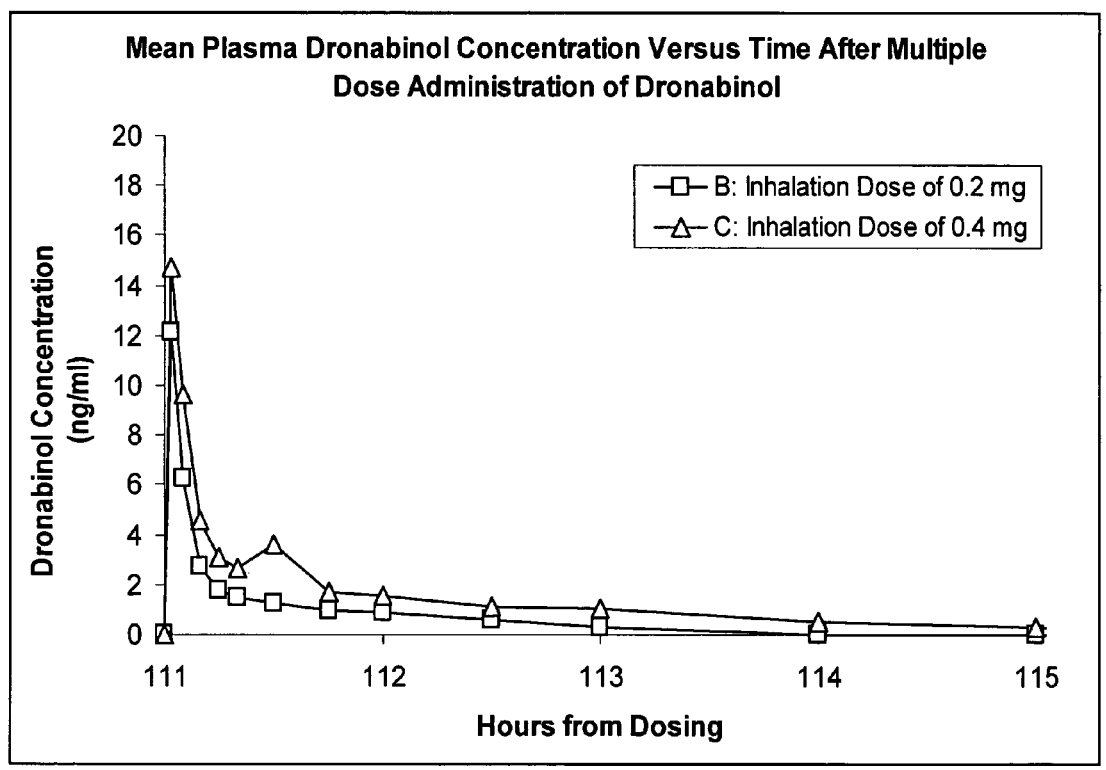
FIGS. 1C and 1D are graphs showing mean dronabinol plasma concentration versus time for treatments B-C (FIG. 1C) and D-G (FIG. 1D), after multiple dose administration.
Figure 1D:
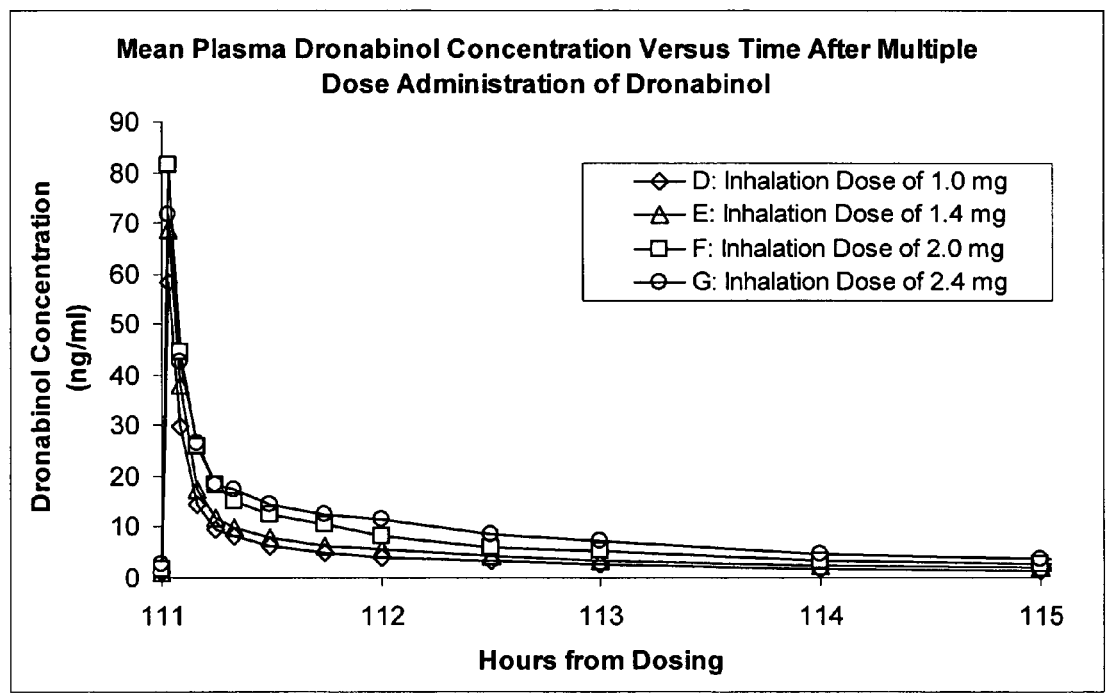
Figure 2A:
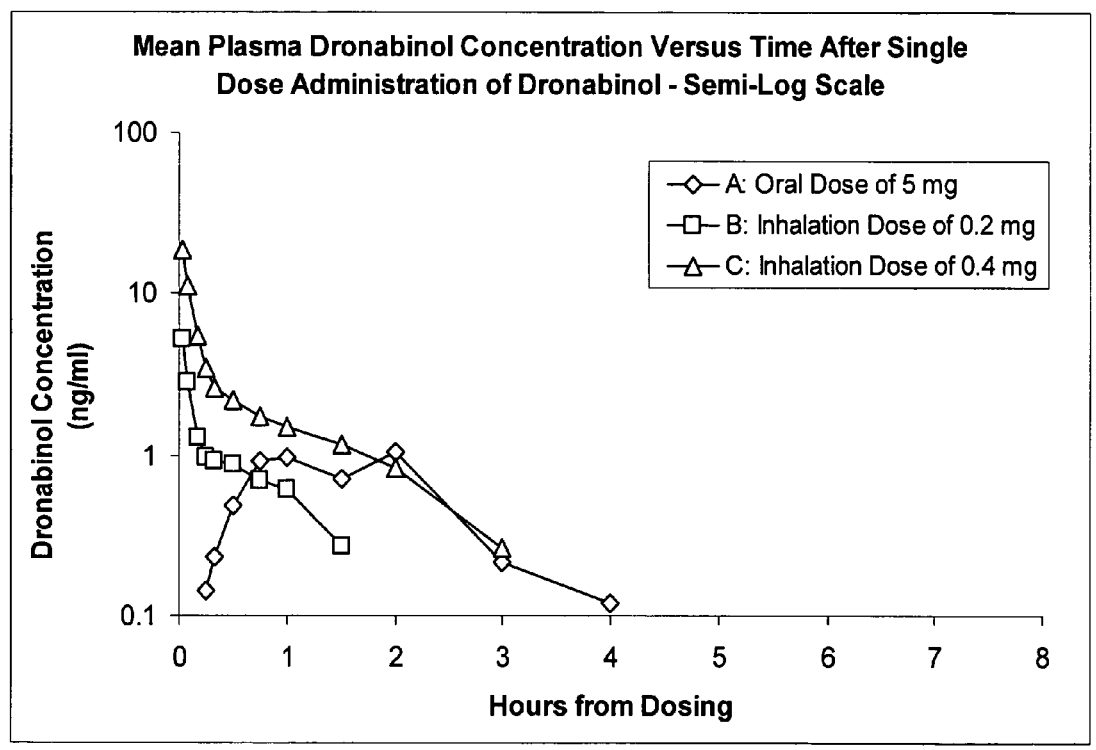
FIG. 2A is a graph showing the mean dronabinol plasma concentration versus time on a semi-log scale after single dose administration of treatments A, B and C.
Figure 2B:
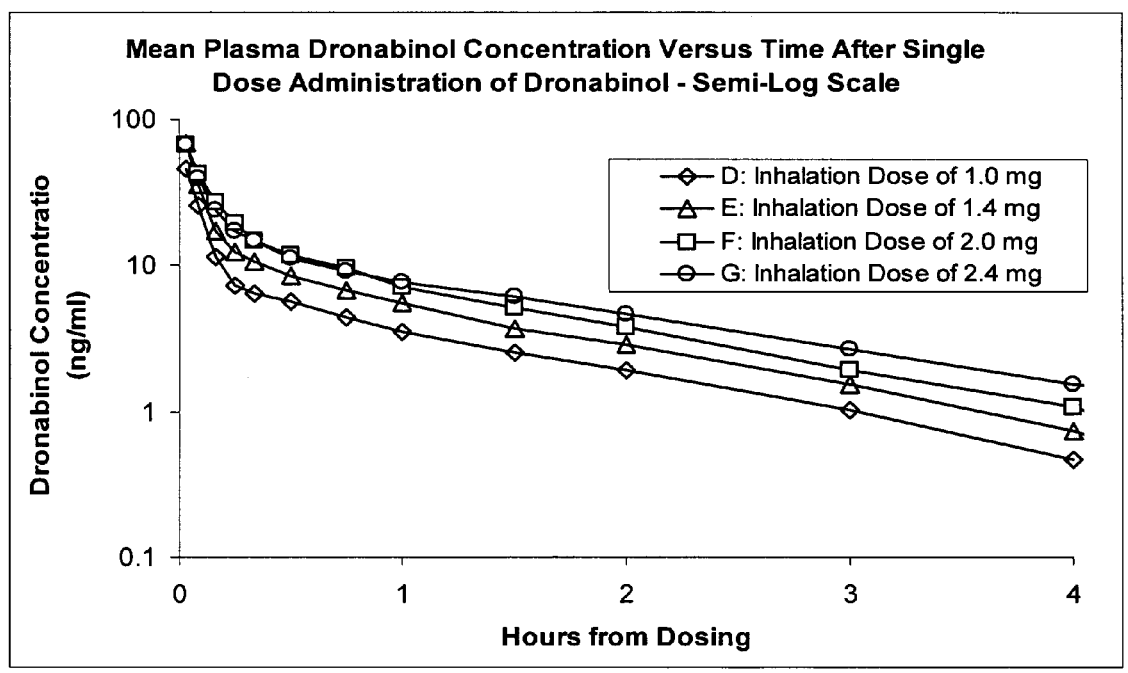
FIG. 2B is a graph showing the mean dronabinol plasma concentration versus time on a semi-log scale after single dose administration of treatments D, E, F and G.
Figure 2C:
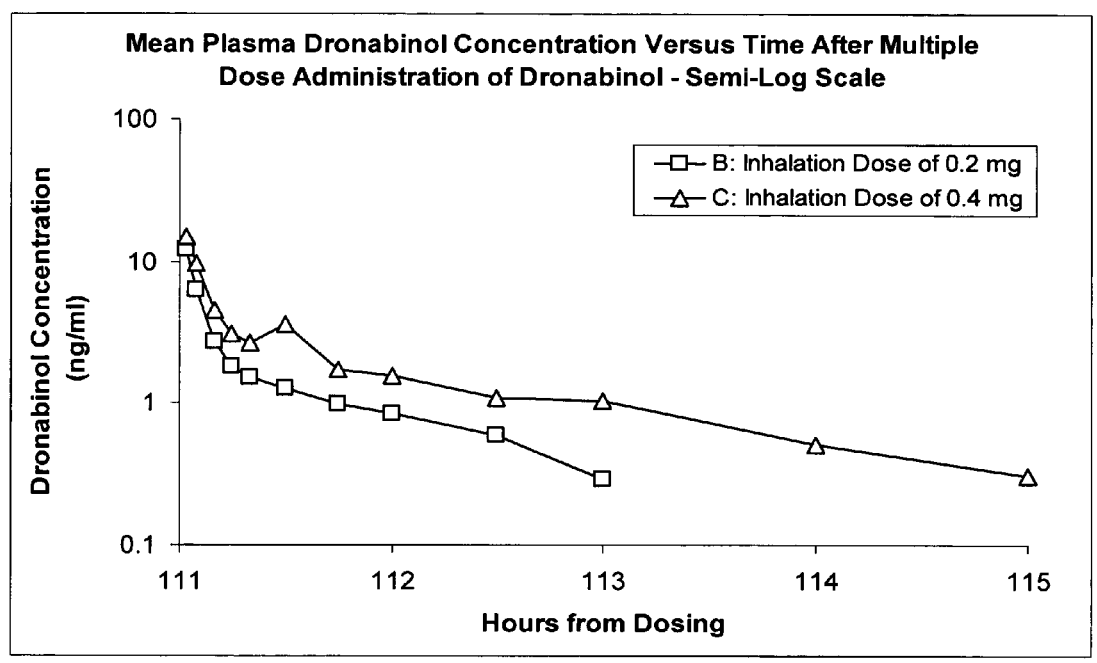
FIG. 2C is a graph showing the mean dronabinol plasma concentration versus time on a semi-log scale, after multiple dose administration of treatments B and C.
Figure 2D:
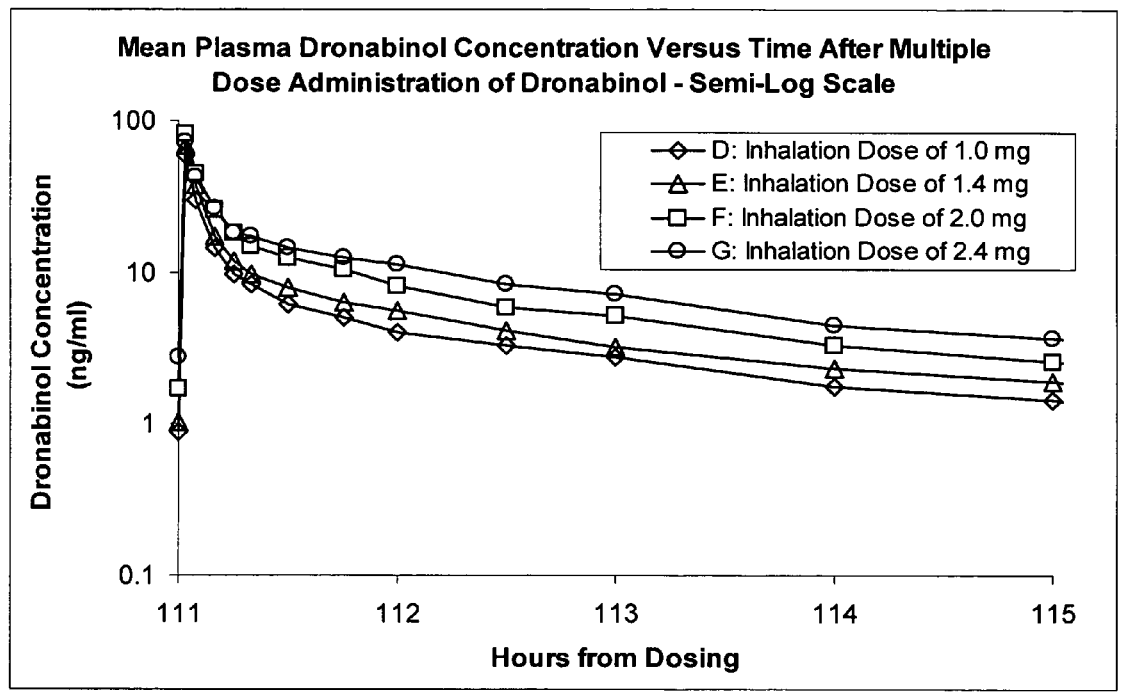
FIG. 2D is a graph showing the mean dronabinol plasma concentration versus time on a semi-log scale, after multiple dose administration of treatments D, E, F and G.
Figure 3:
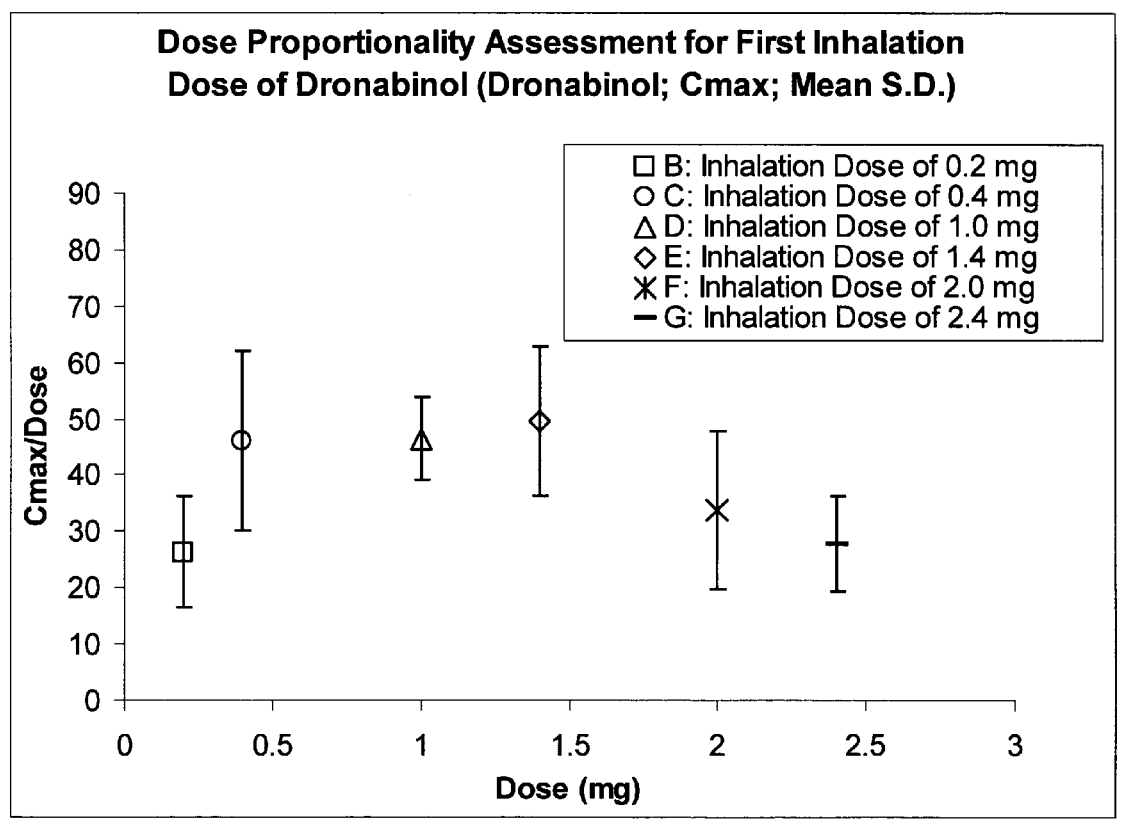
FIG. 3 is a graph showing dose proportionality assessment following deep-lung inhalation dosing (Treatments B-G) for plasma dronabinol of the First Dose (Day 1) illustrating Cmax/Dose vs. Dose.
Figure 4:
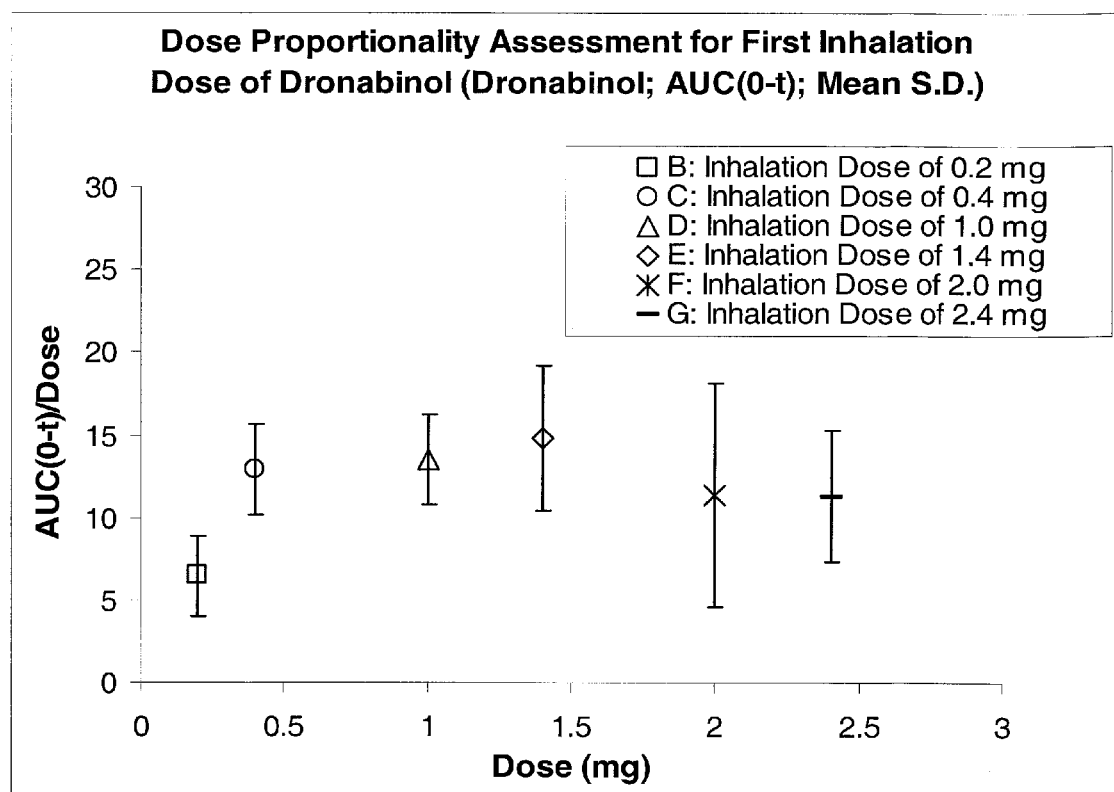
FIG. 4 is a graph showing dose proportionality assessment following deep-lung inhalation dosing for plasma dronabinol of the First Dose (Day 1) illustrating AUC(0-t)/Dose vs. Dose.
Figure 5:
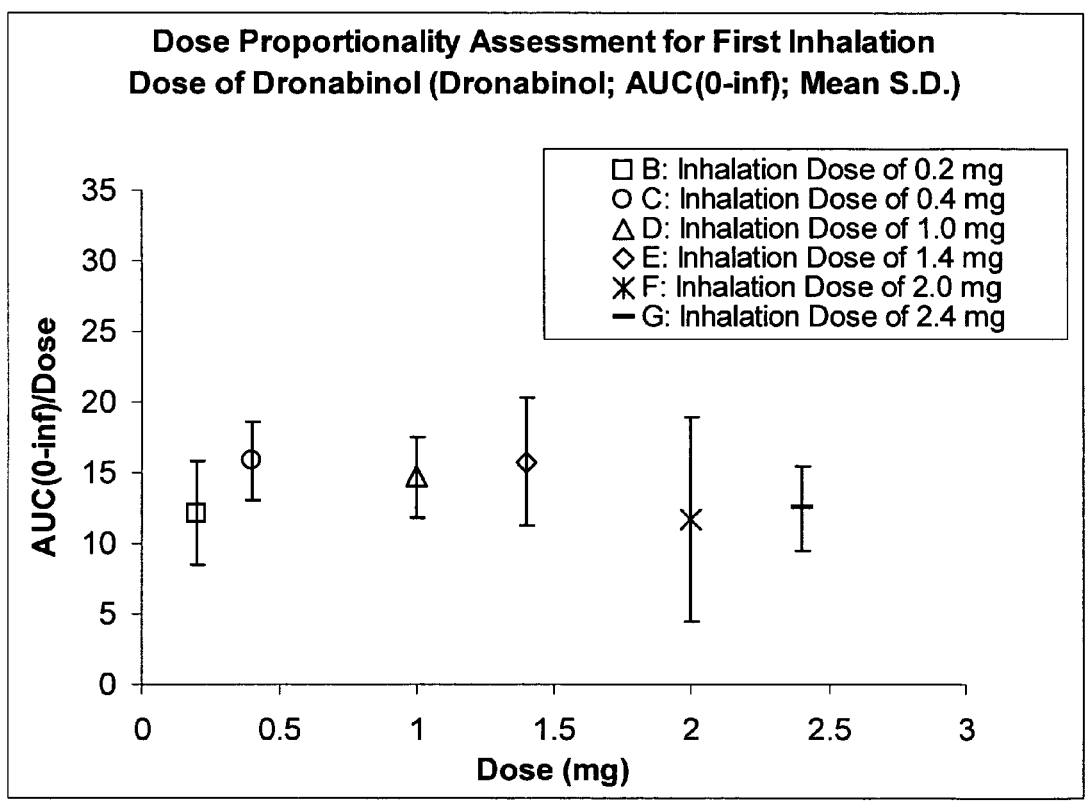
FIG. 5 is a graph showing dose proportionality assessment following deep-lung inhalation dosing for plasma dronabinol of the First Dose (Day 1) illustrating AUC(0-inf)/Dose vs. Dose.
Figure 6:
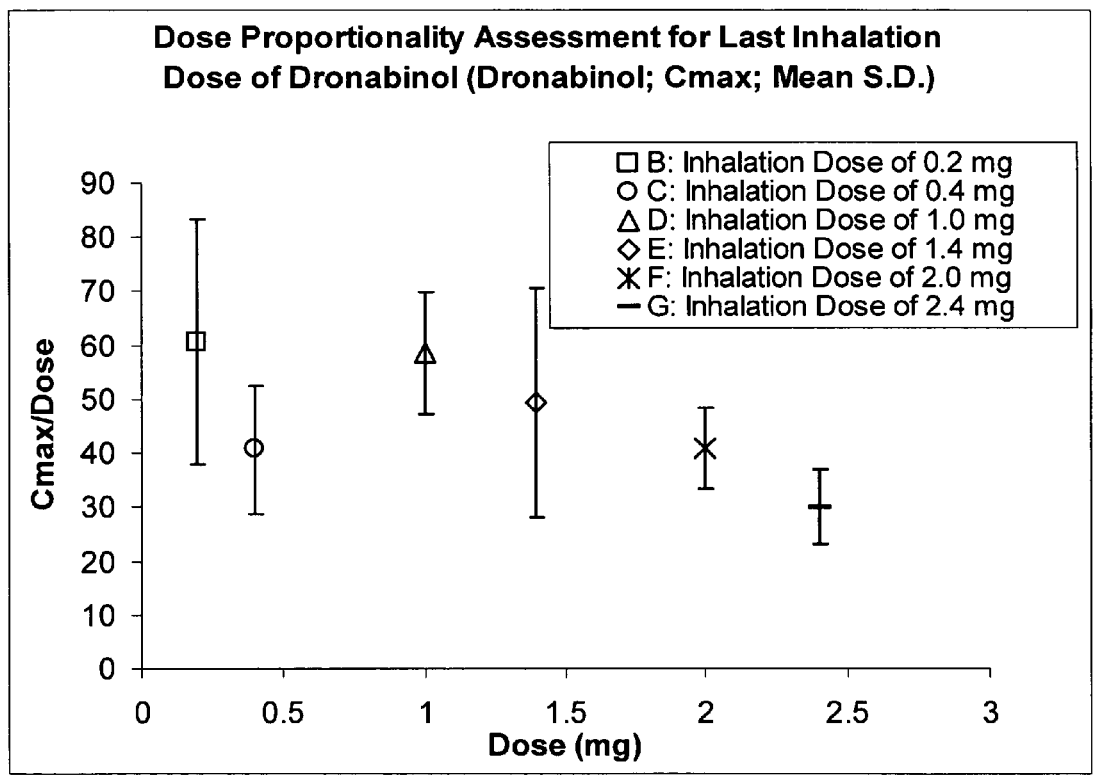
FIG. 6 is a graph showing dose proportionality assessment following deep-lung inhalation dosing for plasma dronabinol of the Last Dose (Day 5) illustrating Cmax/Dose vs. Dose.
Figure 7:
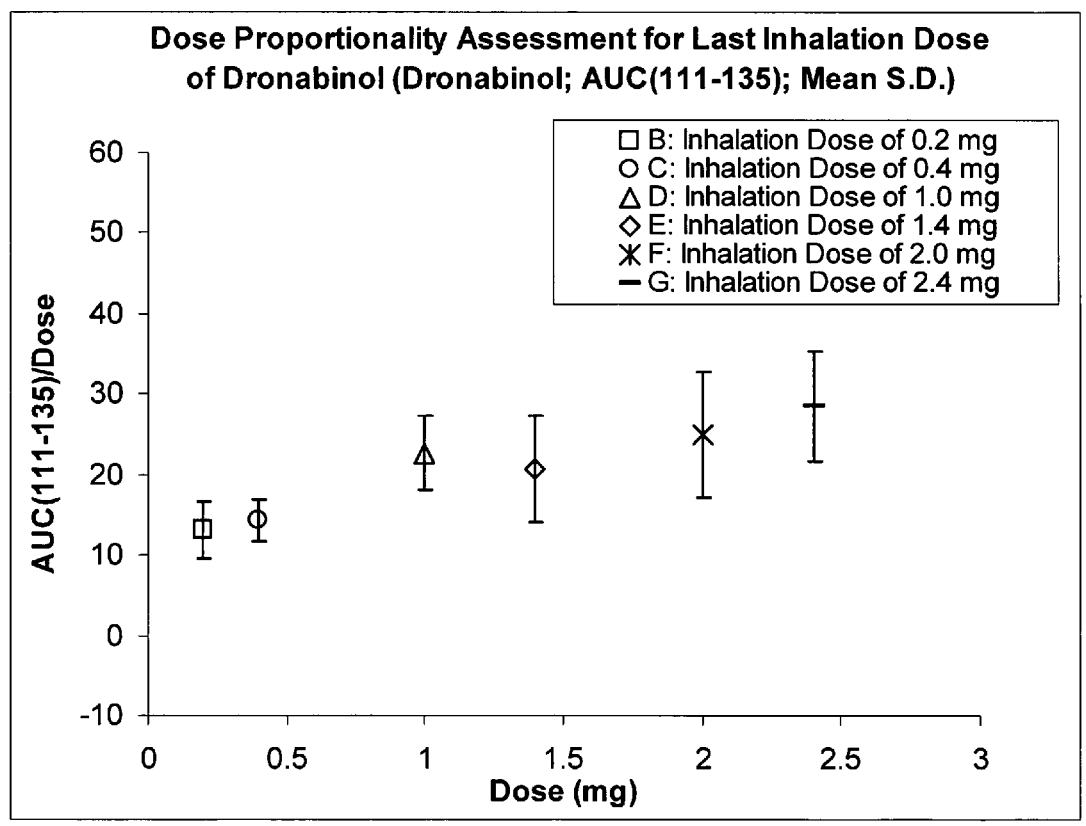
FIG. 7 is a graph showing dose proportionality assessment following deep-lung inhalation dosing for plasma dronabinol of the Last Dose (Day 5) illustrating AUC(111-135)/Dose vs. Dose.
Figure 8:
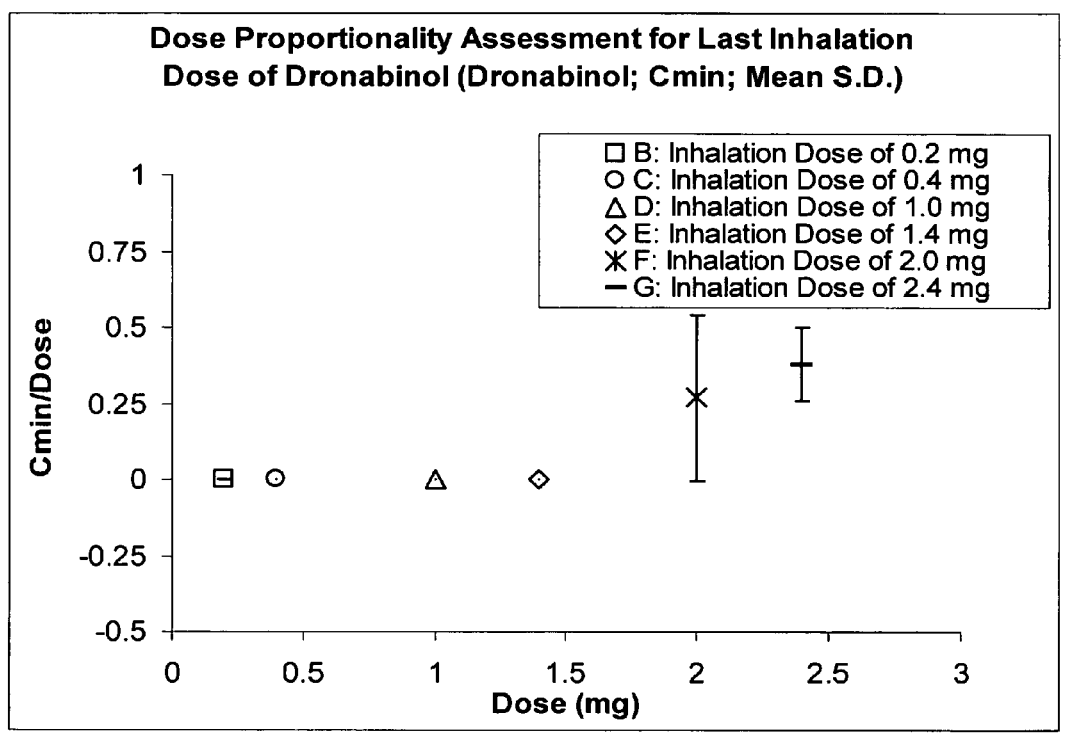
FIG. 8 is a graph showing dose proportionality assessment following deep-lung inhalation dosing for plasma dronabinol of the Last Dose (Day 5) illustrating Cmin/Dose vs. Dose.
Figure 9:
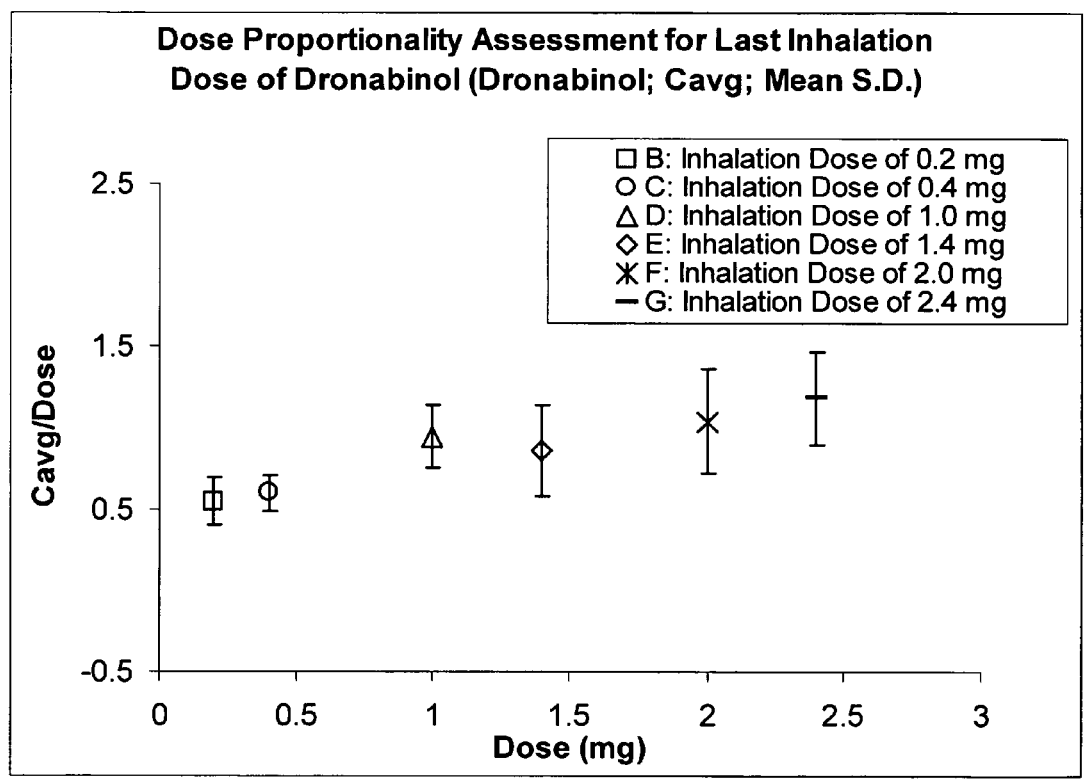
FIG. 9 is a graph showing dose proportionality assessment following deep-lung inhalation dosing for plasma dronabinol of the Last Dose (Day 5) illustrating Cavg/Dose vs. Dose.
Figure 10A:
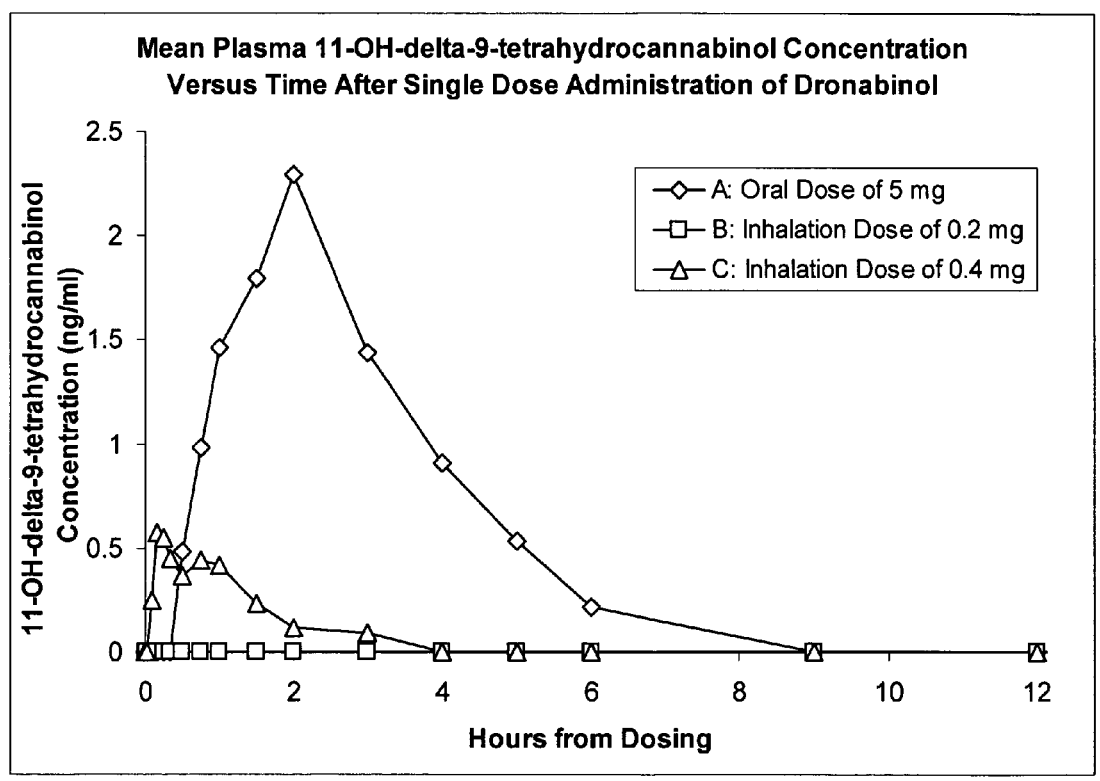
FIGS. 10A-10D are graphs showing mean 11-OH-delta-9-THC plasma concentration versus time on a linear scale after single dose administration of treatments A, B and C (FIG. 10A), treatments D, E, F and G (FIG. 10B), and after multiple dose administration of treatments B and C (FIG. 10C), and treatments D, E, F and G (FIG. 10d).
Figure 10B:
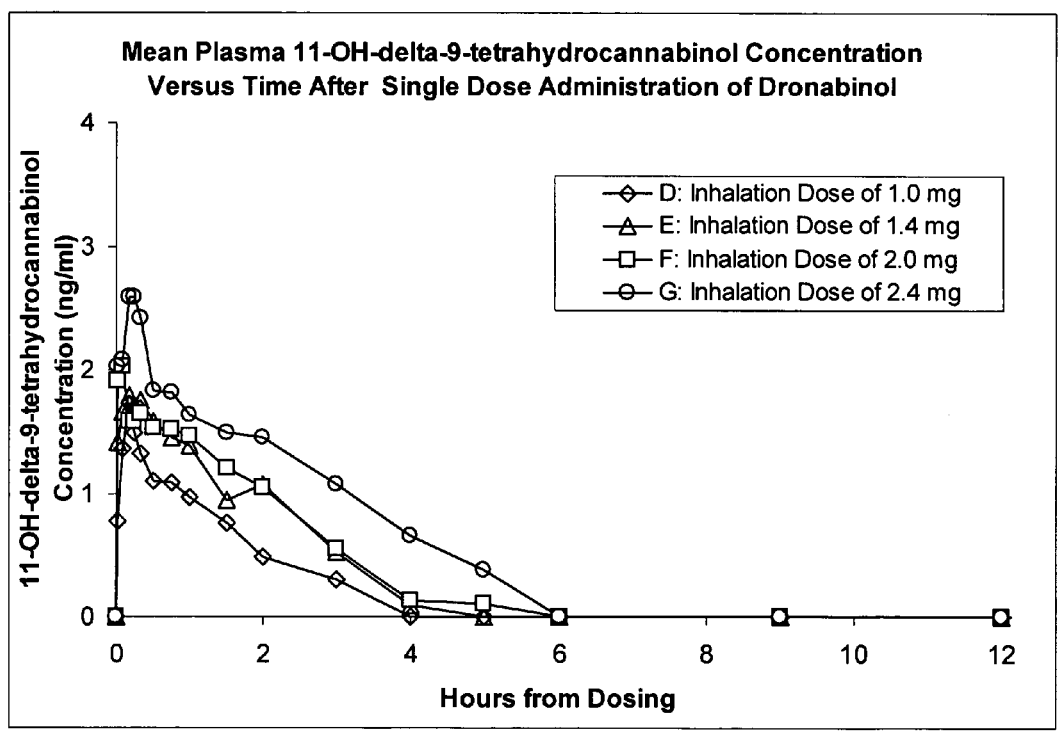
Figure 10C:
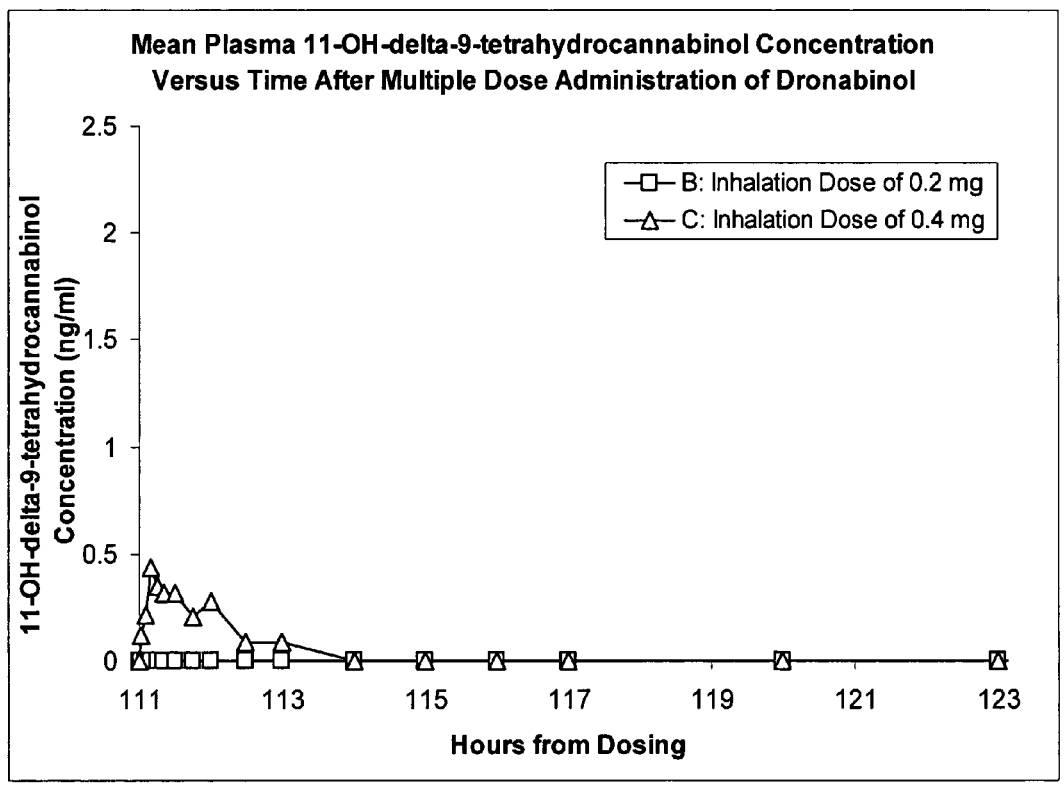
Figure 10D:
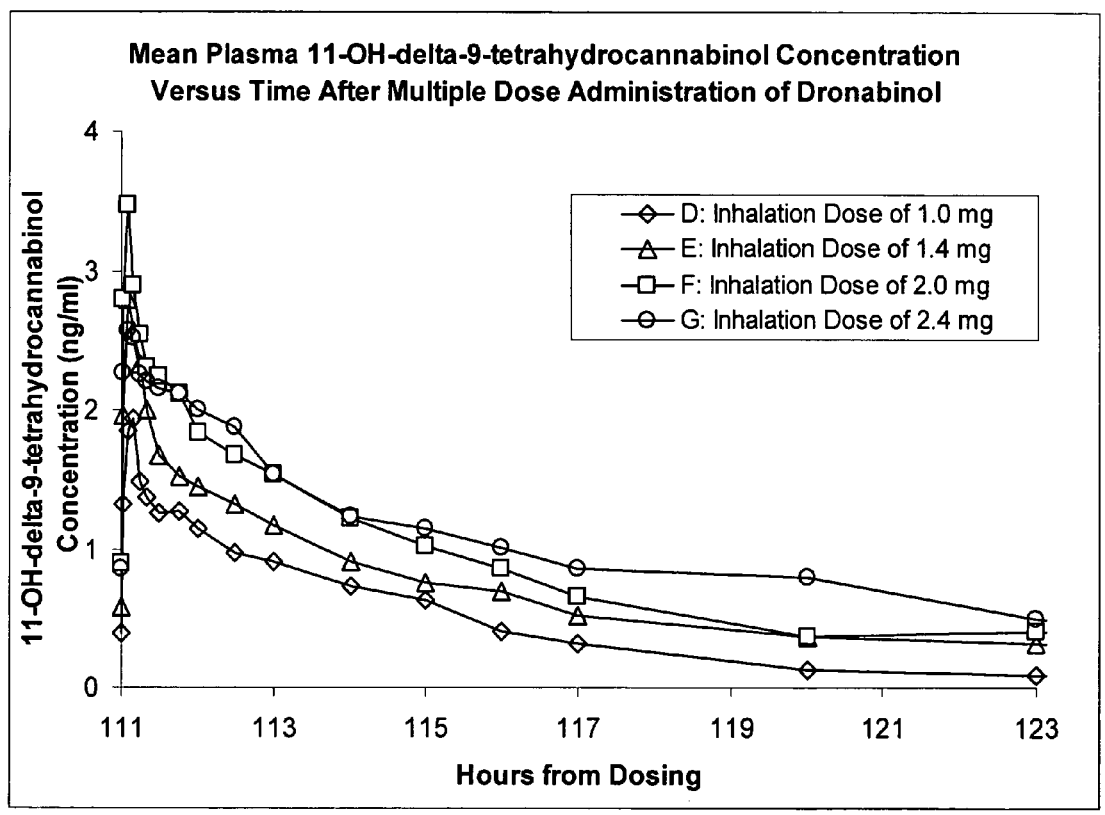
Figure 11:
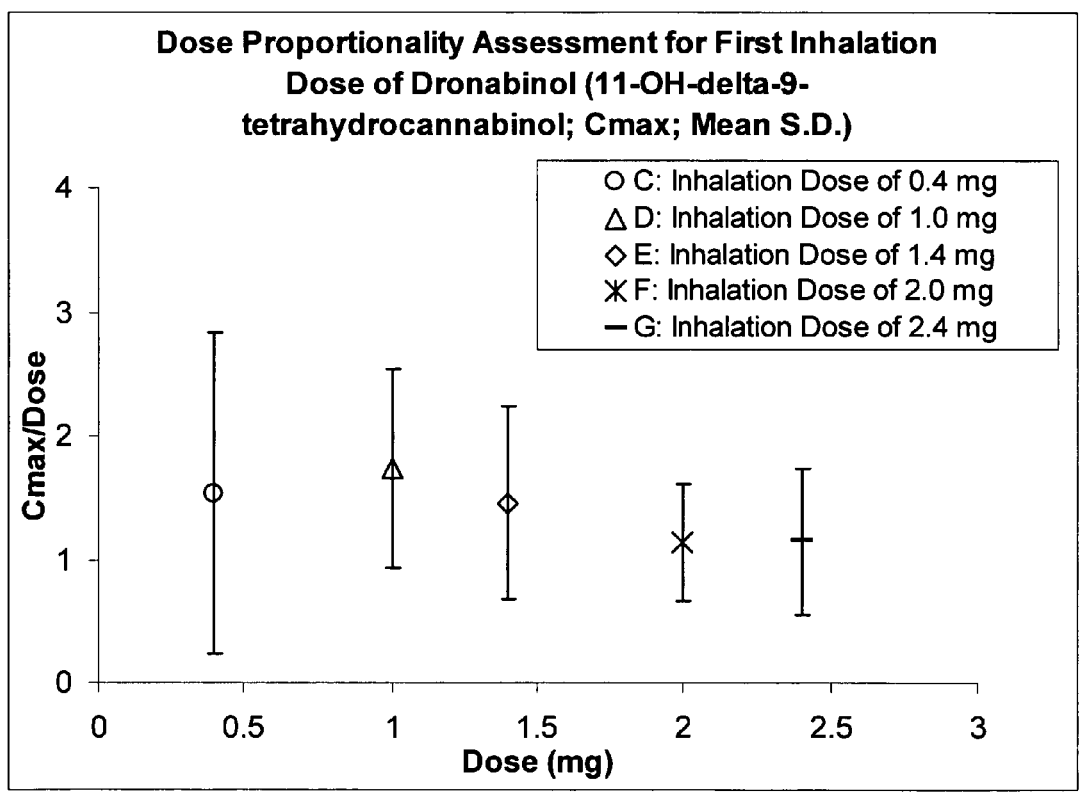
FIG. 11 is a graph showing dose proportionality assessment following deep-lung inhalation dosing for plasma 11-OH-delta-9-THC of the First Dose (Day 1) illustrating Cmax/Dose vs. Dose.
Figure 12:
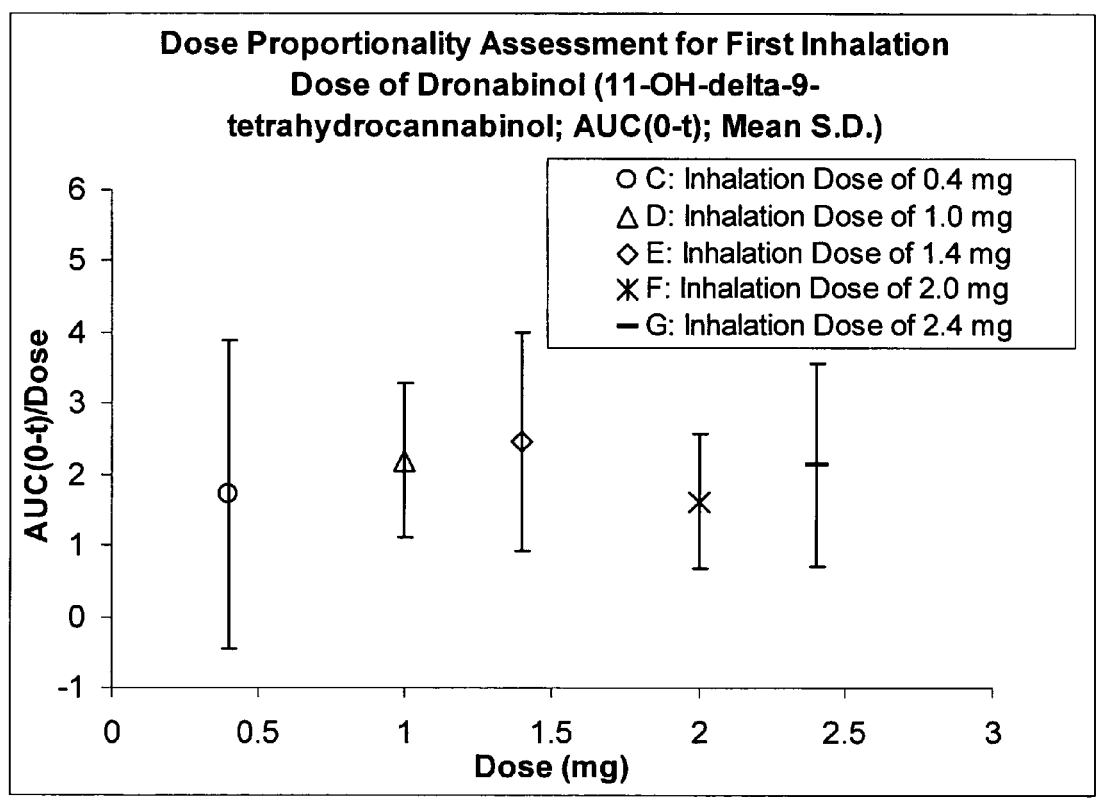
FIG. 12 is a graph showing dose proportionality assessment following deep-lung inhalation dosing for plasma 11-OH-delta-9-THC 1 of the First Dose (Day 1) illustrating AUC(0-t)/Dose vs. Dose.
Figure 13:
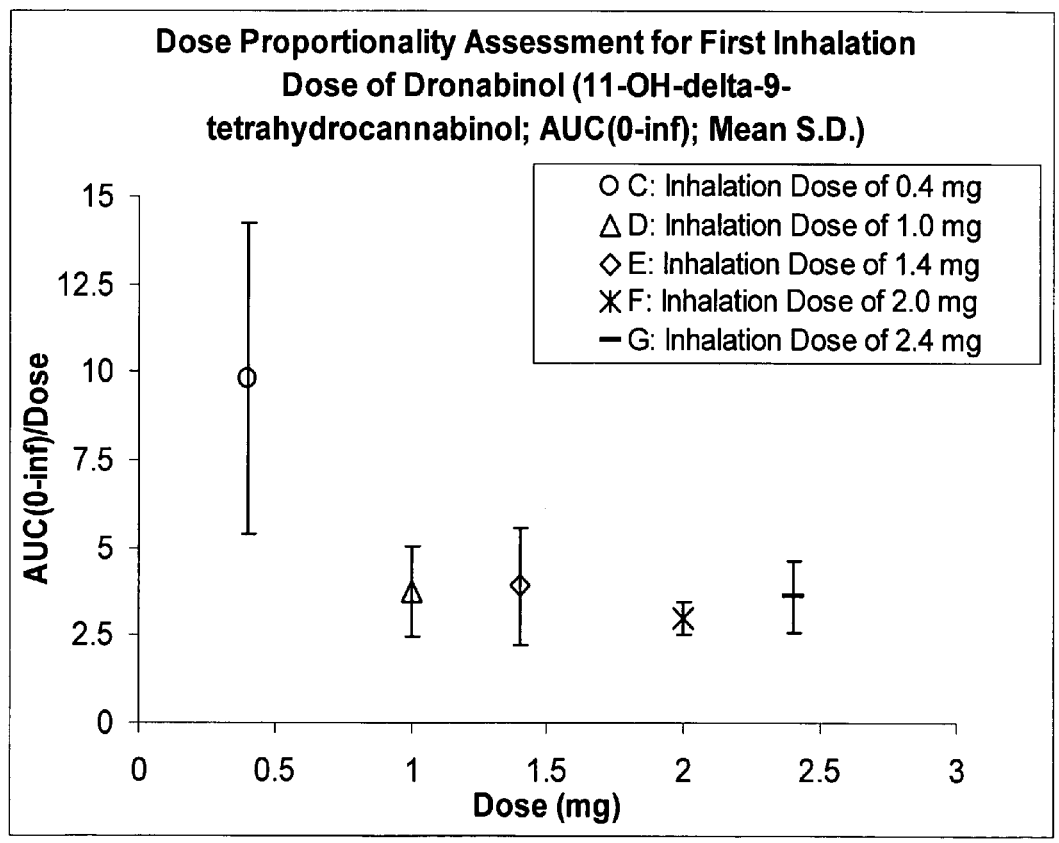
FIG. 13 is a graph showing dose proportionality assessment following deep-lung inhalation dosing for plasma 11-OH-delta-9-THC of the First Dose (Day 1) illustrating AUC(0-inf/Dose vs. Dose.
Figure 14:
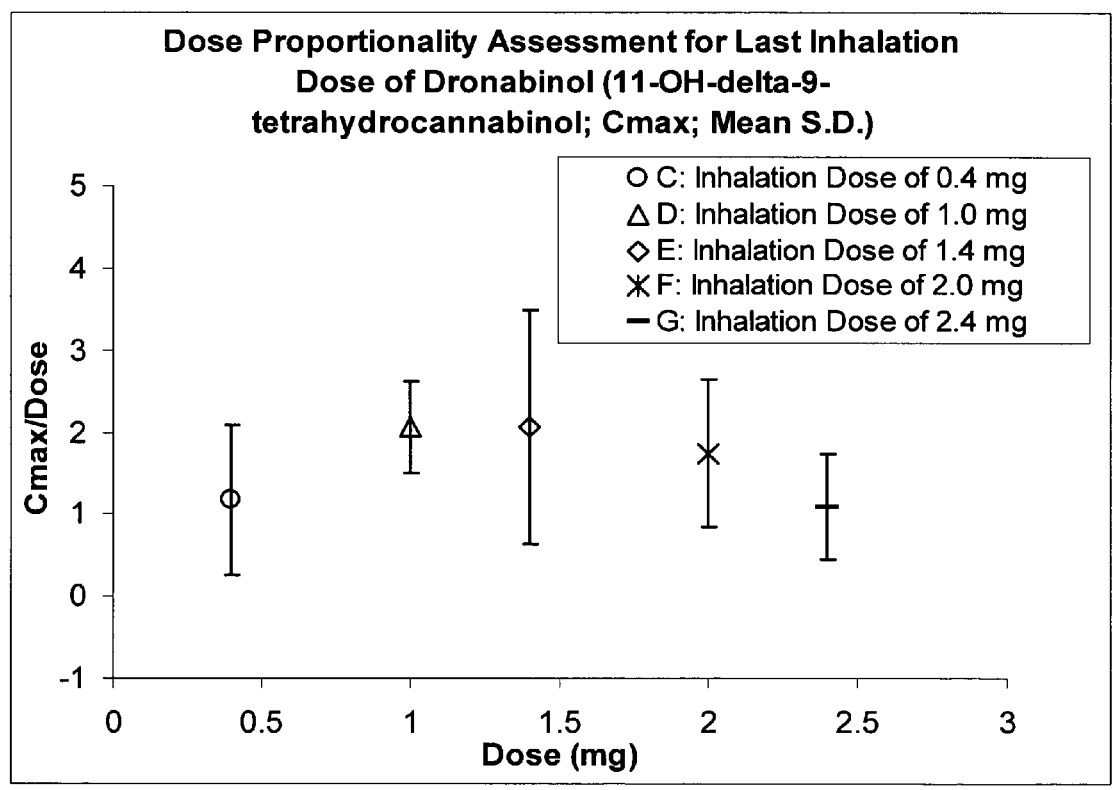
FIG. 14 is a graph showing dose proportionality assessment following deep-lung inhalation dosing for plasma 11-OH-delta-9-THC of the Last Dose (Day 5) illustrating Cmax/Dose vs. Dose.
Figure 15:
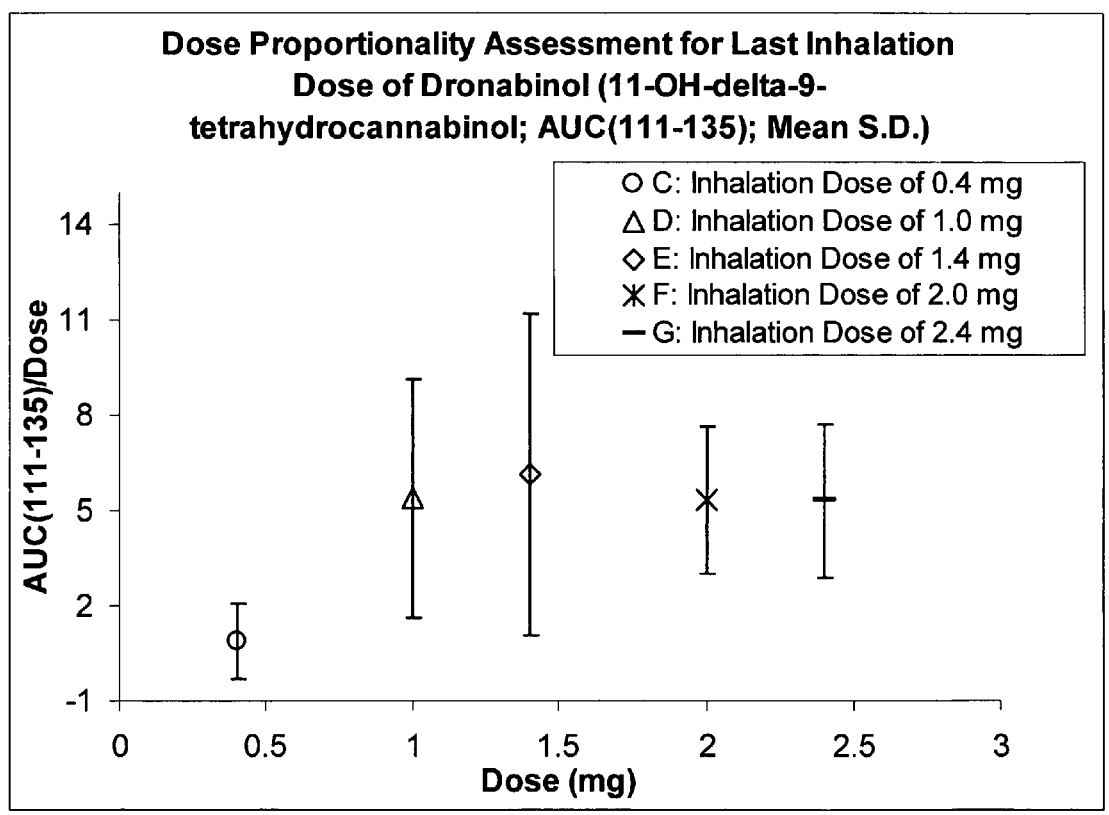
FIG. 15 is a graph showing dose proportionality assessment following deep-lung inhalation dosing for plasma 11-OH-delta-9-THC of the Last Dose (Day 5) illustrating AUC(111-135)/Dose vs. Dose.
Figure 16:
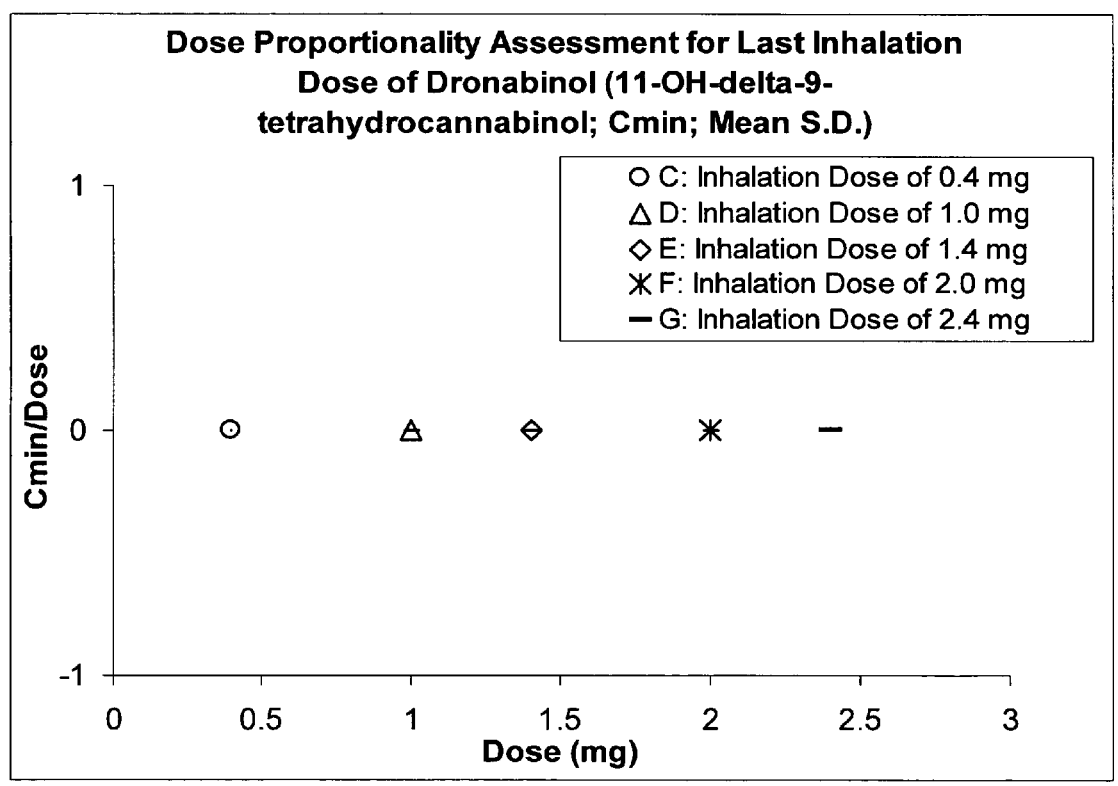
FIG. 16 is a graph showing dose proportionality assessment following deep-lung inhalation dosing for plasma 11-OH-delta-9-THC of the Last Dose (Day 5) illustrating Cmin/Dose vs. Dose.
Figure 17:
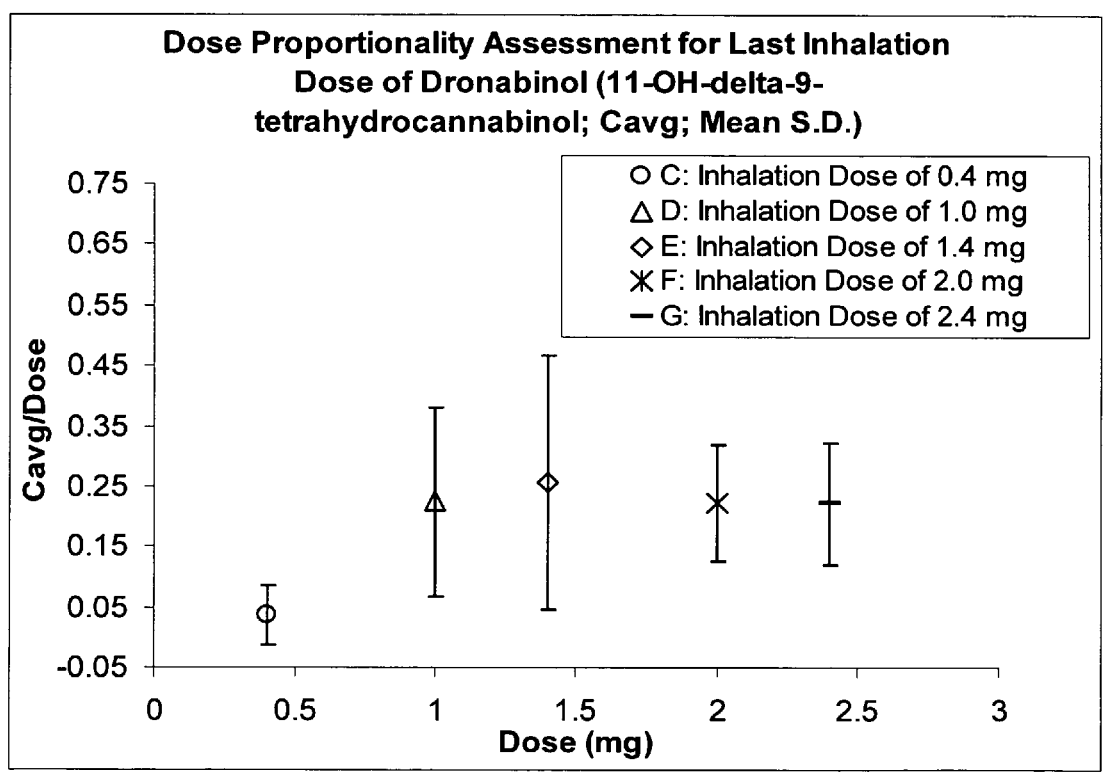
FIG. 17 is a graph showing dose proportionality assessment following deep-lung inhalation dosing for plasma 11-OH-delta-9-THC of the Last Dose (Day 5) illustrating Cavg/Dose vs. Dose.
Figure 18A:
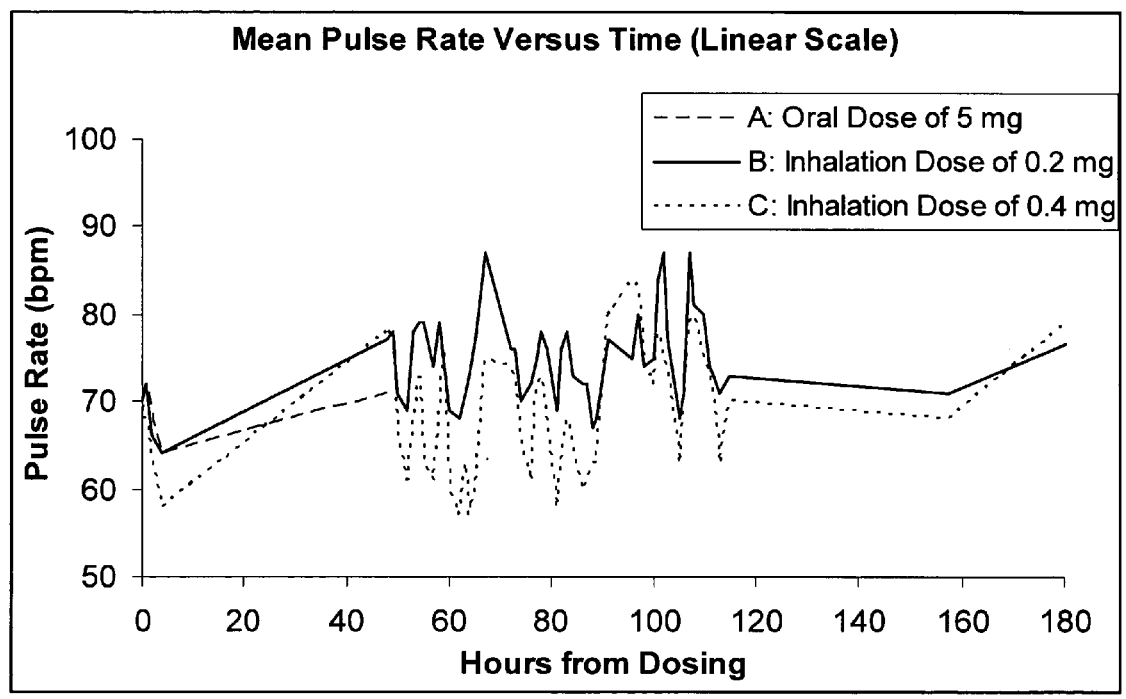
FIGS. 18A-18C are graphs showing mean pulse rate versus time on a linear scale for treatments A, B and C (FIG. 18A), treatments D and E (FIG. 18B), and treatments F and G (FIG. 18C).
Figure 18B:
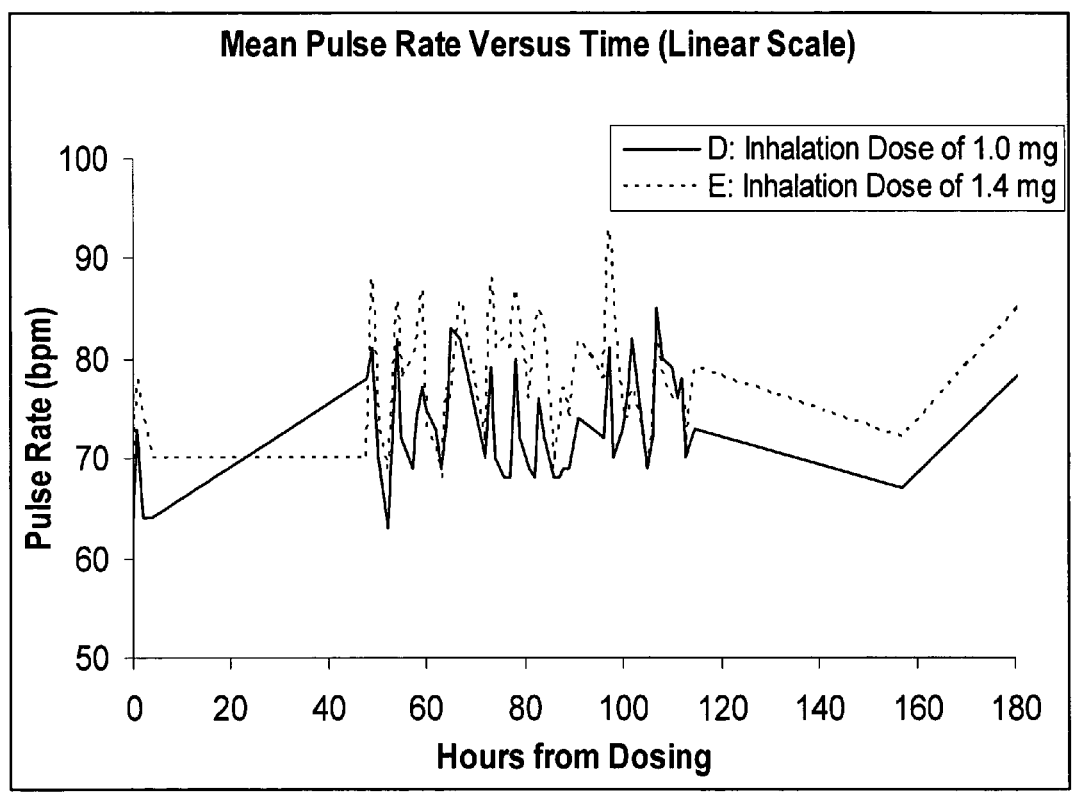
Figure 18C:
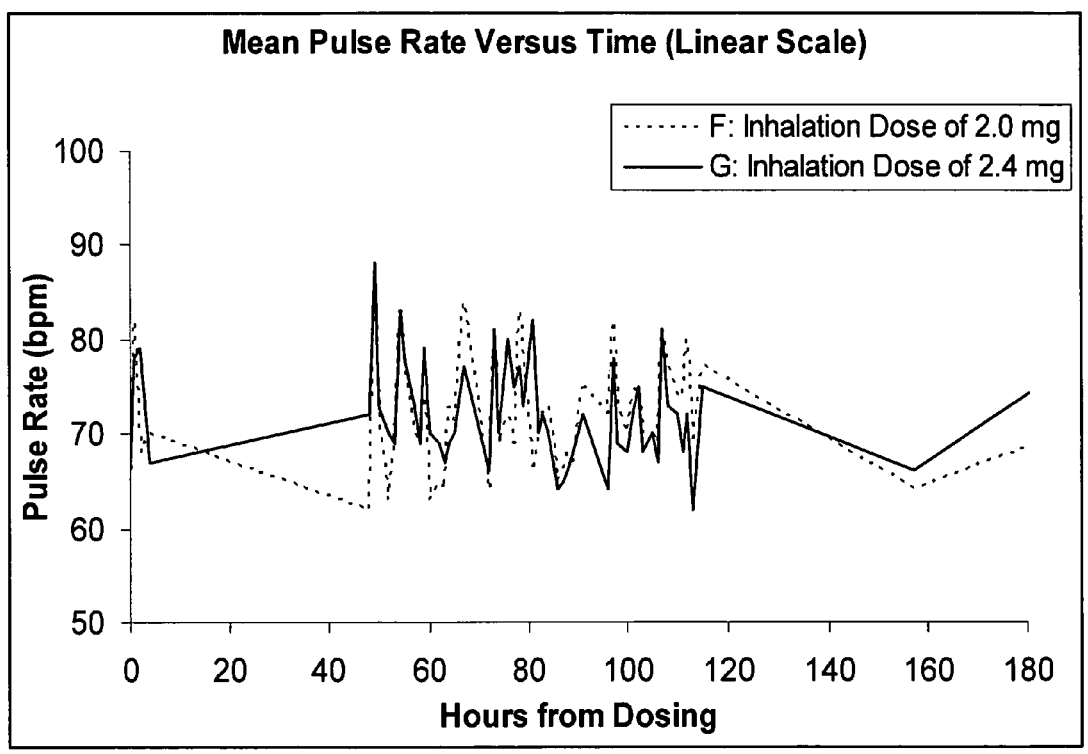
Figure 19A:
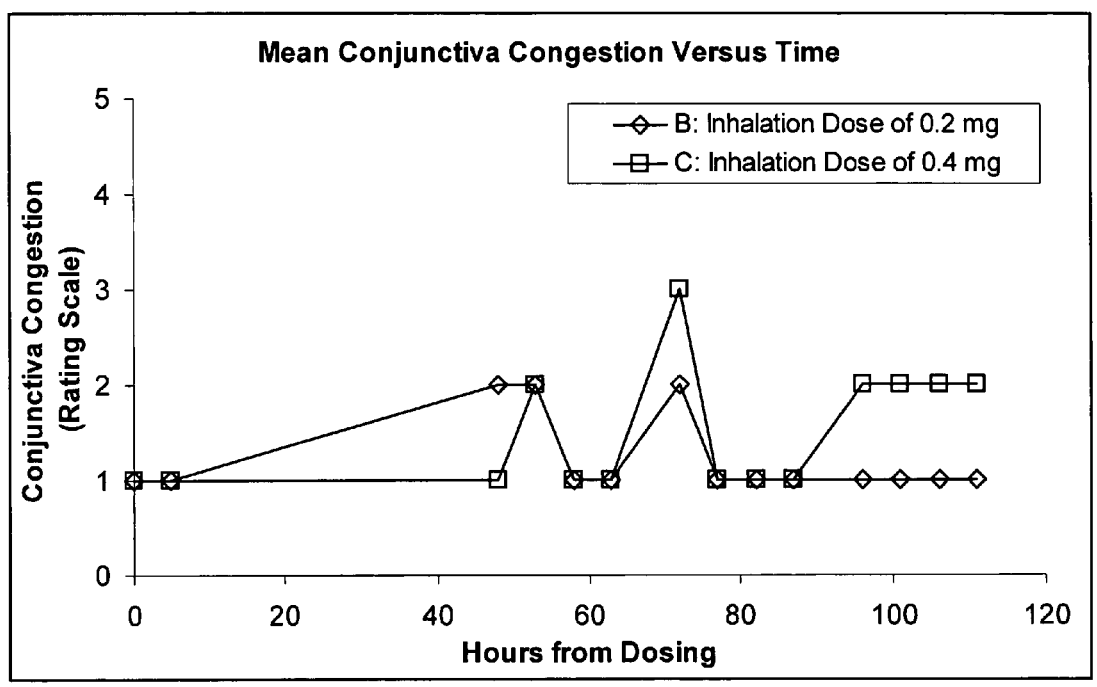
FIGS. 19A-19C are graphs showing mean conjunctiva congestion scores versus time presented in a linear state for treatments B and C (FIG. 19A), treatments D and E (FIG. 19B), and treatments F and G (FIG. 19C).
Figure 19B:
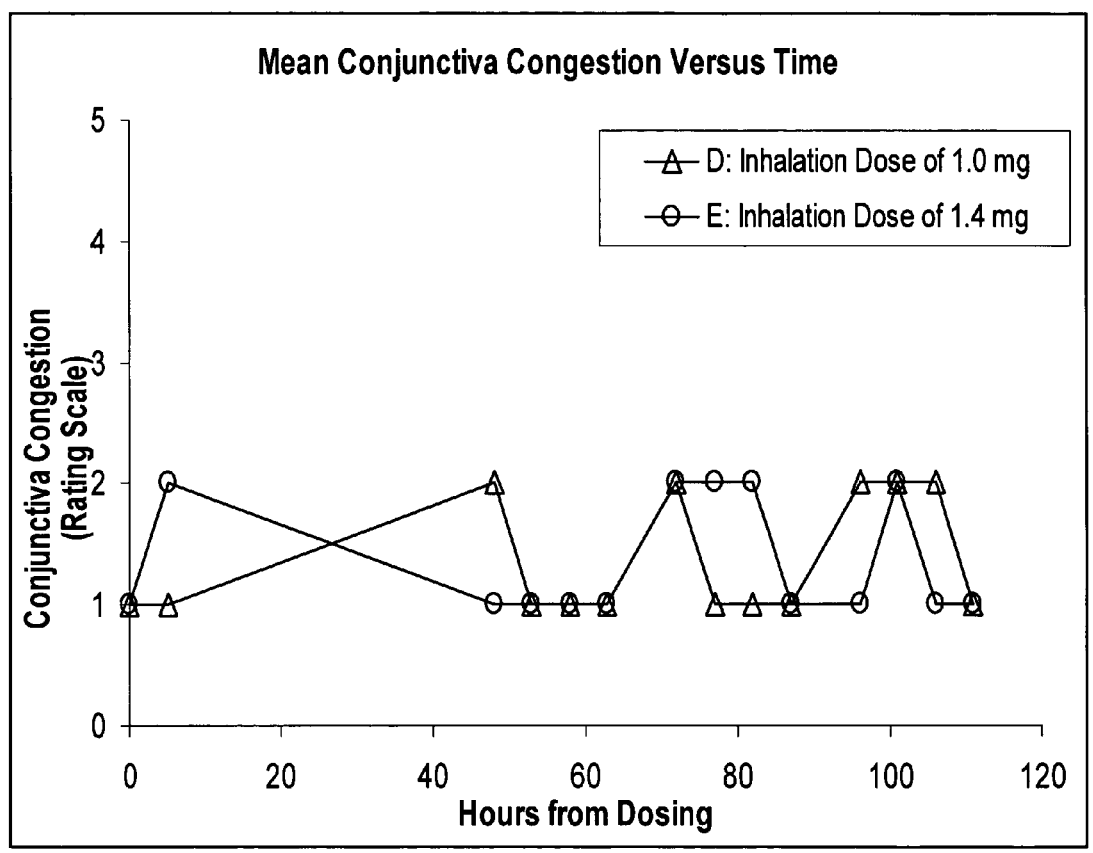
Figure 19C:
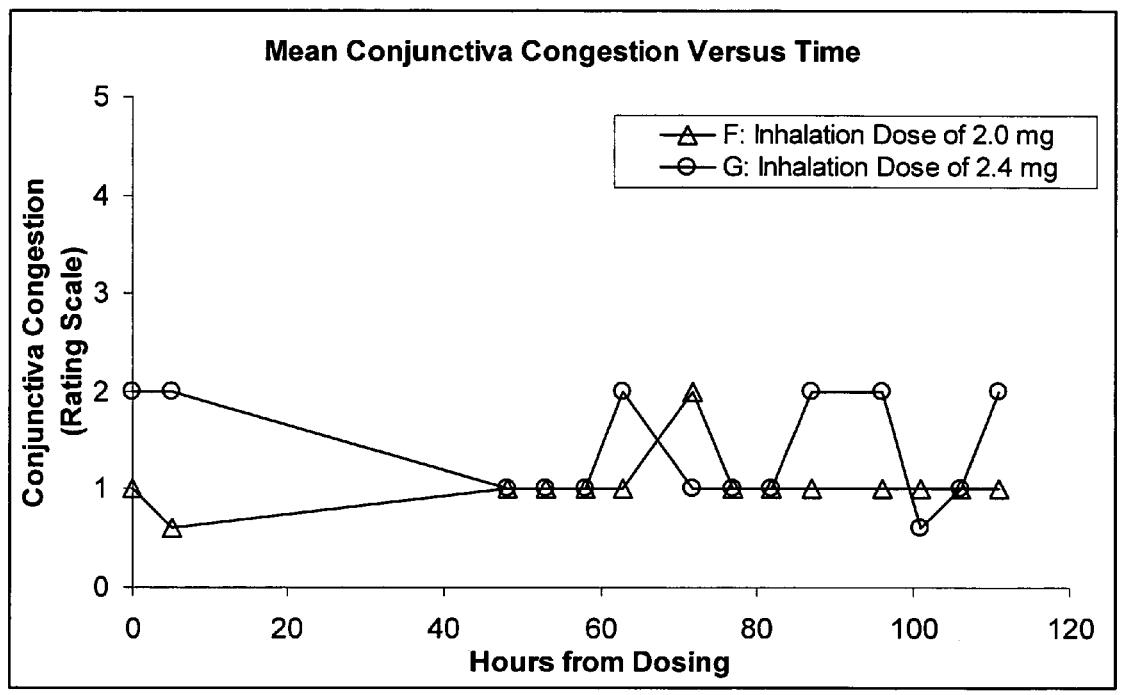

Numerous experiments have shown that the drug formulation is critical for delta-9-tetrahydrocannabinol to be effectively delivered to the lung rapidly. It has been discovered that effective formulations must be stable, aerosolized to a particle size less than or equal to 10 μM to reach the lung, and the drug must readily partition out of the delivery system in order to transport across biological membranes and reach the blood stream. The physico-chemical characteristics of delta-9-tetrahydrocannabinol raw drug material lend themselves to various formulations, including solutions. Delta-9-tetrahydrocannabinol is virtually insoluble in water (0.003 g/mL). It is known that the drug substance is extremely lipophilic, with a reported oil/water coefficient of 9,400,000 (Garret and Hunt, *Journal of Pharmaceutical Sciences*, Vol. 63, No. 7, pages 1056-1064, 1974; and Thomas et al., *The Journal of Pharmacology and Experimental Therapeutics*, Vol. 255, No. 1, pages 624-630, 1990). These factors have been considered in developing the compositions of this invention.

Also critical to the present invention is the need for selecting substances, which will release the drug for absorption or partition it from the dosage form. The lipophilic nature of delta-9-tetrahydrocannabinol suggests that formulations made primarily of lipophilic excipients such as oils, for example, sesame seed oil, currently approved for oral unit dosage use, would not be desirable because the drug would not partition readily. In the case of oily excipients, delta-9-tetrahydrocannabinol would have a strong affinity for the formulation and would slowly partition out, resulting in slow absorption, exactly the problem sought to be avoided.

Semiaqueous solutions, that is, combinations of organic solvents with small, effective amounts of water, lend themselves to making formulations with delta-9-tetrahydrocannabinol with unexpected increases in partitioning, apparently because the drug has a poor affinity for the water within the formulation. Because of the increased ease of partitioning, once released deeply in the lung from the dosage forms of the present invention, delta-9-tetrahydrocannabinol is able to cross cell membranes rapidly, traverse the alveolar epithelial cells, interstitium, and endothelium to reach the blood stream (Thompson, "Pharmacology of Therapeutic Aerosols" Chapter 2, in *Pharmaceutical Inhalation Aerosol Technology*, Ed. Hickey, Marcel Dekker, Inc. New York, pages 29-37,1992). As a further advantage, the formulations of delta-9-tetrahydrocannabinol and semiaqueous solvents of the present invention may be aerosolized more easily than oil based systems.

As will be shown hereinafter, delta-9-tetrahydrocannabinol readily dissolves in ethanol and in equal parts of ethanol and propylene glycol to form clear solutions which, for purposes of the present invention, are "stable," that is, remain clear through three cycles of freeze/thaw. Such compositions, however, do not meet the ease of partitioning required by the present invention because the delta-9-tetrahydrocannabinol prefers to stay in the organic phase and only slowly releases itself from the dosage form at the intended site of absorption. As described in detail below, water can be added to the organic phase, and the delta-9-tetrahydro-cannabinol is able to remain in solution, near the solubility point of the drug, and, unexpectedly, partitioning is enhanced and in vivo bioavailability is accelerated, especially in comparison with intravenous administration of the same formulation. The experiments have also shown that as the water content of the semiaqueous solvent increases and the ethanol content decreases beyond a certain level, the drug readily falls out of solution, and such unstable formulations no longer function as dosage forms within the scope of the invention.

The citation to Thomas, mentioned above, teaches that aerosol particle size has an influence on the deposition pattern of many drugs in the lung. In general, deposition is successful at a mean mass median aerodynamic diameter in the range of from about 1 µM to about 10 µM. For best results in lung delivery, it is known from Thomas that delta-9-tetrahydrocannabinol should be targeted for delivery deep in the lung, and this is facilitated by using aerosol particle diameters of less than about 3 µM, a size which is readily, but unexpectedly, obtained with the compositions of the present invention, using conventional nebulizers, as will be shown in the examples which follow, and in conventional metered dose inhalers.

In one embodiment of the invention, the delta-9-tetrahydrocannabinol comprises from about 0.1 to about 300 mg/mL. The delta-9-tetrahydrocannabinol can comprise any suitable amount, such as, e.g., about 0.1, about 0.5, about 1, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, and about 300 mg/mL.

In one embodiment, the solvent comprises ethanol, water and propylene glycol. In one embodiment, the volumetric ratios of ethanol:water:propylene glycol are selected from those in the range of from about: 10-70:10-30:20-80, respectively, having a combined total of 100.

In one embodiment, the volumetric ratios of ethanol:water:propylene glycol are selected from those in the range of from 10-70:10:20-80, respectively, having a combined total of 100.

In one embodiment, the volumetric ratios of ethanol:water:propylene glycol are 35:10:55, respectively, having a combined total of 100.

The solvent can comprise any suitable solvent or combination of solvents. In one embodiment, the solvent comprises an alcohol, such as, for example, ethanol. The solvent can comprise any suitable amount of alcohol, such as, e.g., about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69% and about 70% alcohol (v/v).

In one embodiment, the solvent comprises a glycol. The glycol can be any suitable glycol, such as, e.g., propylene glycol. The solvent can comprise any suitable amount of glycol, such as, e.g., about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79% and about 80% glycol (v/v).

In one embodiment, the solvent comprises water. In one embodiment, the solvent comprises a suitable amount of water to bring to total percentage of ingredients in the solvent to 100%. In this embodiment, the amount of water in the solvent will be determined by the amount of other components in the solvent. For example, in one embodiment, the solvent comprises 35% ethanol and 55% propylene glycol. In this case, the amount of water to bring the total percentage to 100% would be 10%.

The solvent can comprise any suitable amount of water, such as, e.g., about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29% and about 30% water (v/v).

In one embodiment of the present invention 1-250 mg of delta-9-tetrahydrocannabinol (dronabinol) is dissolved per mL of final composition in USP in 5-95% v/v of ethanol, USP (190 proof), or an obvious equivalent, e.g., isopropanol, in a suitable mixer. Next, add 20-80% v/v propylene glycol, USP, or an obvious equivalent, such as polypropylene glycol, polyethylene glycol, and the like, and 10-25% v/v purified water and mix, and then filter and transfer to a storage tank. A suitable concentration of delta-9-tetrahydro-cannabinol in pharmaceutical compositions for inhalation is 0.05 to 15% (by weight).

In another embodiment of the present invention, the concentration of delta-9-THC is from 0.02 to 5%. Another illustrative embodiment of the present invention is a concentration from 0.1 to 4%. In yet another embodiment of the present invention the formulations of the invention can also include minor but effective amounts of anti-oxidants, surfactants, buffers, sodium chloride, pH adjusting agents, bacteriostats, stabilizers, preservatives, and the like.

In one embodiment of the present invention, the formulations are transferred by conventional means to unit-dose or multi-dose sealed containers, such as ampules and vials, preferably made of amber glass Types I, II and III, with a suitable liner.

The quantity of delta-9-tetrahydro-cannabinol can vary widely. For example, in one embodiment of the present invention the amount may be from about 0.001 to about 35 mg/kg of body weight administered one to six times per day. The dose administered to an animal, such as a human, should be sufficient to effect a therapeutic response over a reasonable time frame. The dose will be determined by the strength of the particular compositions employed and the condition of the subject, as well as the body weight of the subject to be treated. The size of the dose also will be determined by the existence, nature and extent of any adverse side effects that might accompany the administration of a particular composition. An illustrative dosage of delta-9-tetrahydrocannabinol for administration by inhalation is about 0.01 to 100 about mg/kg per day, given in 2-4 divided doses. Yet another illustrative example is dosage of about 0.01 to about 35 mg/kg per day. A third, illustrative example of the present invention is a dosage of about 0.05 to about 5 mg/kg per day. Any suitable amount of delta-9-THC can be administered, such as, e.g., about 0.001 mg, about 0.005 mg, about 0.01 mg, about 0.05 mg, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg or more.

EXAMPLES

The following examples illustrate the present invention. They are not to be construed to limit the claims in any manner whatsoever. Semiaqueous solvent ratios are volumetric, i.e., v/v, and total 100 parts.

Examples 1-7

The physical stability of delta-9-tetrahydrocannabinol in varying ratios of ethanol, USP, purified water and propylene glycol was determined by placing 0.3 ml of delta-9-tetrahydrocannabinol (standard, 100 mg/mL) in a 16×100 mm Pyrex tube, adding 2.7 mL of absolute ethanol for a total volume of 3.0 mL, and shaking the tube until mixed. This resulted in a 100:0:0 ethanol (E); water (W): propylene glycol (PG) ratio and a drug concentration of 10 mg/mL. The foregoing steps were repeated for 12 more ratios according to Table 1 below, which lists volumes of standard delta-9-tetrahydrocannabinol (delta-9-THC), ethanol (Alcohol), purified water (Water), and propylene glycol, and the visual inspection results recorded after the samples are placed on a freeze/thaw (F/T) cycle for three turns.

TABLE 1

Delta-9-THC in Solvent Systems

| Example | Ratio (v/v) (Alcohol:Water: Polypropylene Glycol) | Visual Observation after 3 F/T cycles |
|---|---|---|
| 1A* | 100:0:0 | Clear |
| 1B* | 50:0:50 | Clear |
| 1 | 70:10:20 | Clear |
| 2 | 60:10:30 | Clear |
| 3 | 50:10:40 | Clear |
| 4 | 40:10:50 | Clear |
| 5 | 30:10:60 | Clear |
| 5 | 10:10:80 | Clear/oil droplets form when shaken |
| 6 | 60:20:20 | Clear |
| 7 | 40:20:40 | Clear |
| 7A* | 20:20:60 | Clear/oil droplets form when shaken |
| 7B* | 30:25:45 | Cloudy/oil droplets visible |
| 7C* | 35:30:35 | Cloudy |

[1]Prepared by sequential dilution of Example 11.
*Comparison - 1A and 1B are not semiaqueous solvents and 5A, 7A, 7B and 7C are not stable after freeze/thaw.

As can be seen from Table 1, in varying ratios of ethanol/propylene glycol, delta-9-tetrahydrocannabinol is able to remain in solution in the presence of controlled amounts of water. However, as the water content increases and ethanol content decreases beyond a certain level, the drug readily falls out of solution.

Examples 8-14

The procedure of Examples 1-7 was repeated to assess solubility of increasing concentration of delta-9-tetrahydrocannabinol in a selected vehicle. Based on freeze/thaw data generated with delta-9-tetrahydrocannabinol using different solvent ratios (Table 1) a vehicle comprised of alcohol/water/propylene glycol in a volumetric ratio of 35:10:55 was selected. This ratio allows for good solubility of the drug while keeping the alcohol concentration low enough for ease of manufacturing. Results of the experiments are set forth in Table 2 below.

TABLE 2

Solubility of Delta-9-tetrahydrocannabinol in
Alcohol:Water:Propylene Glycol (35:10:55) (v/v)

| Example | Delta-9-THC Conc. | Visual Observation |
|---|---|---|
| 8 | 0.16 mg/mL | Clear, colorless soln. |
| 9 | 0.40 mg/mL[1] | Clear, colorless soln. |
| 10 | 0.80 mg/mL[1] | Clear, colorless soln. |
| 11 | 25 mg/mL | Clear, light yellow soln. |
| 12 | 50 mg/mL | Clear, light yellow soln. |
| 13 | 75 mg/mL | Clear, light yellow soln. |
| 14 | 100 mg/mL | Clear, light yellow soln. |
| 14A* | 200 mg/mL | Cloudy, yellow soln. |

[1]Prepared by sequential dilution of Example 11.
*Comparative Example (fails to enhance partionability)

The results illustrate that if the alcohol concentration is reduced below approximately 35%, drug droplets begin to form indicating that the drug is below its solubility point in the vehicle. The results also indicate that delta-9-tetrahydrocannabinol concentrations in excess of 100 mg/mL are able to be manufactured with this formulation, but 200 mg/mL cannot. From ease of manufacturing and expected doses of delta-9-tetrahydrocannabinol required for inhalation, a drug concentration of 25 mg/mL in the formulation of Example 8 (35:10:55 Alcohol:Water:Propylene Glycol) was evaluated in preclinical studies. A Pari LC Plus Nebulizer was used in a conventional fashion and it generated aerosolized particles having a mean mass median aerodynamic diameter of 2.96 ηM.

Two animal species, rat and dog, were administered the formulation in a 14 day multiple dose inhalation study with a nebulizer. Results from the pharmacokinetic portion of the study indicated comparability between $t_{max}$ values found for intravenous and inhaled delivery. $T_{max}$ values are summarized for both single (intravenous and inhalation) and for multiple dose (intraveneous and inhalation) of delta-9-tetrahydrocannabinol in Table 3, as follows:

TABLE 3

Animal Studies of Exposure to Inhaled Delta-9-Tetrahydrocannabinol
in Alcohol:Water:Propylene Glycol (35:10:55) (v/v)

Single Dose Administration

| Species | Route of Admin. | Dose | Duration of Exposure | Average $t_{max}$ (minutes) | App. Calc. $t_{max}$ (minutes) |
|---|---|---|---|---|---|
| Dog | IV | 1 mg/kg | — | 1.8 | 1.8 |
|  | Inhalation | 2 mg/kg | 8 minutes | 15.6 | 7.6 |
| Rat | IV | 2 mg/kg | — | 2.1 | 2.1 |
|  | Inhalation | 0.5 mg/kg | 1.25 minutes | 5.7 | 4.45 |
|  | Inhalation | 4.8 mg/kg | 15 minutes | 33.3 | 18.3 |

Multiple Dose Inhalation

| Species | Route of Admin.[2] | Dose | Duration of Exposure | Average $t_{max}$ (minutes) | App. Calc. $t_{max}$ (minutes) |
|---|---|---|---|---|---|
| Dog | IV | 1 mg/kg | — | 1.8 | 1.8 |
|  | Inhalation | 2 mg/kg | 8 minutes | 10.2 | 2.2 |
|  | Inhalation | 5 mg/kg | 20 minutes | 22.2 | 2.2 |
|  | Inhalation | 15 mg/kg | 60 minutes | 66 | 6 |
| Rat | IV | 2 mg/kg | — | 2.1 | 2.1 |
|  | Inhalation | 2 mg/kg | 5 minutes | 6 | 1 |
|  | Inhalation | 5 mg/kg | 15 minutes | 17.4 | 2.4 |
|  | Inhalation | 15 mg/kg | 45 minutes | 46.2 | 1.2 |

[1]Apparent $t_{max}$ calculated as ($t_{max}$ – duration of exposure). Blood samples drawn after entire dose is administered.
[2]IV data represents single dose administration.

The data in the foregoing examples show that a semiaqueous formulation of delta-9-tetrahydrocannabinol in accordance with the present invention can produce a stable clear solution near the solubility point of the drug. Moreover, because delta-9-tetrahydrocannabinol has poor affinity for the formulation, it is able to partition out and transport across cell membranes to reach the bloodstream rapidly. This has been demonstrated by the comparative $t_{max}$ values achieved in single dose intravenous and 14 day multiple dose inhalation studies as detailed above.

Example 15

This example demonstrates the pharmacokinetics and safety of dronabinol after pulmonary administration.

A. Overall Study Design and Plan

A parallel group, double-blind, randomized, placebo-controlled study of six ascending single and multiple inhalation dose administrations and one single oral dose of dronabinol in healthy male and female subjects. Exclusions included recent tobacco use, marijuana consumption, pulmonary dysfunction or evidence of any significant medical conditions. A total of 56 subjects were enrolled into 7 treatment groups. The treatment groups were as follows:

Treatment A: 5 mg dronabinol (Marinol® oral capsule)
Treatment B: 0.2 mg dronabinol (1 inhalation per dose)
Treatment C: 0.4 mg dronabinol (2 inhalations per dose)
Treatment D: 1.0 mg dronabinol (5 inhalations per dose)
Treatment E: 1.4 mg dronabinol (7 inhalations per dose)
Treatment F: 2.0 mg dronabinol (10 inhalations per dose)
Treatment G: 2.4 mg dronabinol (12 inhalations per dose)

Treatment A consisted of a single oral administration on Day 1. Treatments B through G consisted of a single inhalation on Day 1, followed by daytime inhalations four times daily (every 5 hours, with 9 hours between the last daytime and following first morning dose) on Days 3-5. In each treatment group of 8 subjects, two received placebo and six received dronabinol. 51 subjects completed the study. Seven of 8 subjects completed the Treatment D and Treatment F regimens, and 5 of 8 subjects completed the Treatment G regimen.

Subjects receiving Treatment A were in a fasted state following a 10-hour overnight fast. Subjects receiving Treatments B through G were in a fasted state following a 10-hour overnight fast on Day 1. On Days 3 through 5 the subjects were in a fed state having had breakfast, lunch, dinner, or a snack within 1 hour of dosing.

B. Pharmacokinetics

Blood samples were obtained on Days 1 and 5 at pre-dose, 2, 5, 10, 15, 20, 30, 45 minutes, and 1, 1.5, 2, 3, 4, 5, 6, 9, 12, 24, 36 and 48 hours. After dosing on Day 5, a 72-hour sample was also obtained. Samples were also collected prior to dosing at 53, 58 and 63 hours; prior to dosing at 72, 77, 82 and 87 hours; prior to dosing at 96, 101, 106 and 111 hours and at 111:02, 111:05, 111:10, 111:15, 111:20, 111:30, 111:45 (hr:min) and 112, 112.5, 113, 114, 115, 116 and 117 hours; 120, 123 and 135 hours; 159 hours and 183 hours. Samples from subjects receiving placebo were assayed only at representative timepoints. All subjects receiving placebo had no quantifiable levels of dronabinol or 11-OH-delta-9-THC reported in any of their samples.

Plasma concentrations of delta-9-THC and the 11-OH metabolite (11-OH-delta-9-TCH) were analyzed by Liquid Chromotography/Mass Spectroscopy/Mass Spectroscopy (LC/MS/MS). The limit of quantitation was 0.50 ng/mL.

Pharmacokinetic parameters were determined for dronabinol (delta-9-THC) and its principal active metabolite 11-OH-delta-9-THC.

The analysis was a two-stage procedure. Steady-state was evaluated by regressing the 63-, 87-, and 111-hour dronabinol and 111-OH-delta-9-THC concentrations over time. The 58-, 82-, and 106-hour; 53-, 77-, and 101-hour, and the 48-, 72-, and 96-hour dronabinol and 11-OH-delta-9-THC concentrations were also evaluated by regression. Steady-state was achieved when the slope was not statistically different from zero.

Dose adjusted parameters were analyzed using analysis of variance (ANOVA) with treatment in the model to determine dose proportionality. Dose adjustment was made by dividing the parameter value by the dose (in mg). The 90% confidence intervals about the difference of all painwise comparisons were also created.

The mean (SD) pharmacokinetics parameters for dronabinol after single dose dronabinol administration are presented in Table 4.

TABLE 4

Mean (SD) PK Parameters For Dronabinol After Single Dose Dronabinol Administration (Day 1)

| Parameters | Oral Dose | Nebulized Dose | | | | | |
|---|---|---|---|---|---|---|---|
| | 5 mg (Treatment A) | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| Cmax (ng/mL) | 1.863 (0.80) | 5.259 (1.96) | 18.410 (6.37) | 46.324 (7.32) | 69.133 (18.7) | 73.237 (26.83) | 64.788 (21.9) |
| Tmax (hr)[a] | 0.994 (0.74-2) | 0.037 (0.03-0.04) | 0.036 (0.03-0.06) | 0.032 (0.03-0.04) | 0.033 (0.03-0.04) | 0.041 (0.03-0.08) | 0.039 (0.03-0.05) |
| AUC (0-t) (ng*hr/mL) | 1.807 (1.328) | 1.296 (0.4856) | 5.167 (1.096) | 13.50 (2.693) | 20.77 (6.153) | 27.01 (9.735) | 30.21 (6.579) |
| AUC (0-inf) (ng*hr/mL) | 3.013[b] | 2.422 (0.73) | 6.351 (1.1) | 14.69 (2.84) | 22.01 (6.34) | 28.10 (9.8) | 31.58 (6.63) |
| T 1/2el (hr) | 1.03 | 1.31 (0.488) | 1.21 (0.188) | 1.15 (0.183) | 1.12 (0.232) | 1.06 (0.176) | 1.69 (0.519) |
| Kel (1/hr) | 0.674[b] | 0.576 (0.16) | 0.583 (0.09) | 0.619 (0.11) | 0.644 (0.15) | 0.666 (0.11) | 0.440 (0.12) |
| LN (Cmax) | 0.5486 (0.4175) | 1.607 (0.3489) | 2.867 (0.3260) | 3.825 (0.1644) | 4.207 (0.2625) | 4.241 (0.3630) | 4.119 (0.3741) |
| LN [AUC (0-t)] | 0.3849 (0.7116) | 0.1843 (0.4552) | 1.623 (0.2173) | 2.588 (0.1813) | 2.999 (0.2847) | 3.245 (0.3582) | 5.389 (0.2185) |
| LN [AUC (0-inf)] | 1.103 | 0.8380 (0.3545) | 1.835 (0.1823) | 2.674 (0.1744) | 3.058 (0.2792) | 3.287 (0.3460) | 3.435 (0.2097) |

[a] values presented as median (range)
[b] values represent only one subject

Results after single dose dronabinol administration are further illustrated in FIGS. 1-6 and 26.

The mean (SD) pharmacokinetics parameters for dronabinol after multiple dose dronabinol administration are presented in Table 5.

TABLE 5

Mean (SD) PK Parameters For Dronabinol After Multiple Dose Dronabinol Administration (Day 5)

| Parameters | Nebulized Dose | | | | | |
|---|---|---|---|---|---|---|
| | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| Cmax (ng/mL) | 12.123 (4.54) | 16.241 (4.72) | 58.381 (11.3) | 68.791 (29.8) | 81.507 (15.2) | 71.633 (16.5) |
| Cmin | 0 | 0 | 0 | 0 | 0.539 | 0.907 |

TABLE 5-continued

Mean (SD) PK Parameters For Dronabinol After Multiple Dose Dronabinol Administration (Day 5)

| | Nebulized Dose | | | | | |
|---|---|---|---|---|---|---|
| Parameters | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| (ng/mL) | | | | | (0.55) | (0.29) |
| Tmax (hr)$^a$ | 0.033 (0.03-0.04) | 0.039 (0.03-0.5) | 0.034 (0.02-0.04) | 0.034 (0.03-0.04) | 0.034 (0.03-0.04) | 0.034 (0.03-0.04) |
| Tmin (hr) | 2.38 (0.665) | 4.13 (0.983) | 14.5 (7.45) | 19.0 (7.75) | 24.0 (0.00) | 24.0 (0.00) |
| AUC (111-135) (ng*hr/mL) | 2.616 (0.70) | 5.720 (1.04) | 22.61 (4.64) | 28.90 (9.37) | 49.88 (15.5) | 68.18 (16.6) |
| Cavg (ng*hr/mL) | 0.109 (0.0292) | 0.238 (0.0435) | 0.942 (0.193) | 1.20 (0.390) | 2.08 (0.645) | 2.84 (0.692) |
| FI$^c$ | — | — | — | — | 10254.2 (3028.35) | 8307.32 (3258.99) |
| T 1/2el(hr) | 1.13 (0.269) | 1.73 (0.290) | 3.20 (1.92) | 4.09 (2.14) | 11.4 (11.0) | 20.6 (10.0) |
| Kel (1/hr) | 0.649 (0.18) | 0.410 (0.07) | 0.275 (0.13) | 0.214 (0.12) | 0.103 (0.07) | 0.0381 (0.02) |

$^a$values presented as median (range)
$^b$values represent only one subject
$^c$Fluctuation Index, calculated as: (Cmax − Cmin) × 100/Cmin Results after multiple dose dronabinol administration are further illustrated in FIGS. 7-10 and 28.

The data shows that all inhalation treatments resulted in similar shapes of plasma dronabinol concentration-time profiles with rapidly reached peak concentrations and equally quick decline in post peak concentrations on both Days 1 and 5. On Day 1, the mean Tmax ranged from 0.032 hours (Treatment D) to 0.041 hours (Treatment F), and the mean Cmax ranged from 5.259 ng/mL (Treatment B) to 73.237 ng/mL (Treatment F). On Day 5, the mean Tmax ranged from 0.034 hours (Treatments D-F) to 0.039 hours (Treatment C), and the mean Cmax ranged from 12.123 ng/mL (Treatment B) to 81.507 ng/mL (Treatment F). The mean concentration-time profile for Treatment A, the oral dose, differed from those of the other Day treatments by having a substantially lower mean peak concentration (mean Cmax of 1.863 ng/mL) and longer time to reach the peak (mean Tmax of 0.994 h).

The results of the dose proportionality assessment following deep-lung inhalation dosing for plasma dronabinol are detailed in the following figures: Cmax (FIG. 4), AUC(0-t) (FIG. 5), and AUC(0-inf) (Day 1) (FIG. 6); and last dose Cmax (FIG. 7), Cmin (FIG. 8), AUC(111-135) (FIG. 9), and Cavg (Day 5) (FIG. 10). Dose normalization was based on the total mg dose administered. Following the first (Day 1) dosing, the main effects were significant for Cmax/Dose and for AUC(0-t)/Dose (P-values<0.05), but not for AUC(0-inf)/Dose (P-value=0.4644). Following the last dosing on Day 5, the main effects were not significant for Cmax/Dose (P-value=0.0528) but were significant for Cmin/Dose, AUC (111-135)/Dose, and Cavg/Dose (P-values<0.05).

The mean (SD) pharmacokinetics parameters for 11-OH-THC after single dose dronabinol administration are presented in Table 6.

TABLE 6

Mean (SD) PK Parameters For 11-OH-THC After Single Dose Dronabinol Administration (Day 1)

| | Oral Dose | Nebulized Dose | | | | | |
|---|---|---|---|---|---|---|---|
| Parameters | 5 mg (Treatment A) | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| Cmax (ng/mL) | 2.610 (0.58) | 0 | 0.614 (0.52) | 1.731 (0.81) | 2.032 (1.09) | 2.124 (0.99) | 2.384 (1.2) |
| Tmax (hr)$^a$ | 1.50 (0.99-2) | NR | 0.208 (0.16-0.25) | 0.16 (0.08-0.17) | 0.125 (0.02-0.33) | 0.115 (0.03-0.78) | 0.167 (0.04-0.34) |
| AUC (0-t) (ng*hr/mL) | 6.028 (1.86) | 0 | 0.690 (0.87) | 2.196 (1.09) | 3.434 (2.16) | 3.589 (1.24) | 5.883 (3.2) |
| AUC (0-inf) (ng*hr/mL) | 7.808 (1.46) | NR | 3.917 (1.77) | 3.745 (1.27) | 5.469 (2.31) | 5.984 (0.94) | 8.663 (2.5) |
| T 1/2el (hr) | 1.48 (0.364) | NR | 3.67 (3.22) | 1.79 (0.487) | 1.98 (0.719) | 1.79 (0.557) | 2.04 (0.376) |
| Kel (1/hr) | 0.495 (0.14) | NR | 0.300 (0.20) | 0.408 (0.09) | 0.384 (0.12) | 0.416 (0.13) | 0.347 (0.06) |
| LN (Cmax) | 0.9374 (0.2342) | NR | −0.1162 (0.2998) | 0.4473 (0.5085) | 0.6134 (0.4511) | 0.6684 (0.4628) | 0.7143 (0.6866) |
| LN | 1.748 | NR | −0.2524 | 0.6458 | 1.071 | 1.307 | 1.612 |

TABLE 6-continued

Mean (SD) PK Parameters For 11-OH-THC After Single Dose Dronabinol Administration (Day 1)

| | Oral Dose | Nebulized Dose | | | | | |
|---|---|---|---|---|---|---|---|
| Parameters | 5 mg (Treatment A) | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| [AUC (0-t)] | (0.3612) | | (0.8901) | (0.6404) | (0.6289) | (0.3327) | (0.6837) |
| LN [AUC (0-inf)] | 2.040 (0.2019) | NR | 1.288 (0.4994) | 1.260 (0.4066) | 1.623 (0.4468) | 1.780 (0.1563) | 2.125 (0.3098) |

[a]values presented as median (range)
[b]values represent only one subject
NR missing or not reportable data Results after single dose dronabinol administration are further illustrated in FIGS. 11-15 and 27.

The mean (SD) pharmacokinetics parameters for 11-OH-THC after multiple dose dronabinol administration are presented in Table 7.

The mean concentration-time profile for Treatment A, the oral dose, differed from the other treatments. Although the mean peak concentration for Treatment A (mean Cmax of 2.610 ng/mL) was similar to that of Treatment G, the time to reach the peak was substantially longer (mean Tmax of 1.5 hr)

TABLE 7

Mean (SD) PK Parameters For 11-OH-THC After Multiple Dose Dronabinol Administration (Day 5)

| | Nebulized Dose | | | | | |
|---|---|---|---|---|---|---|
| Parameters | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| Cmax (ng/mL) | 0 | 0.466 (0.38) | 2.059 (0.57) | 2.885 (2.0) | 3.476 (1.8) | 2.610 (1.55) |
| Cmin (ng/mL) | 0 | 0 | 0 | 0 | 0 | 0 |
| Tmax (hr)[a] | NR | 0.208 (0.16-0.5) | 0.162 (0.08-0.18) | 0.089 (0.07-0.17) | 0.084 (0.08-0.01) | 0.167 (0.08-0.75) |
| Tmin (hr) | 0 | 0.494 (1.21) | 8.63 (7.76) | 14.1 (10.8) | 17.4 (9.10) | 20.0 (6.93) |
| AUC (111-135) (ng*hr/mL) | 0 | 0.355 (0.45) | 5.372 (3.76) | 8.580 (7.1) | 10.64 (4.62) | 12.72 (5.79) |
| Cavg (ng*hr/mL) | 0 | 0.0148 (0.0187) | 0.224 (0.157) | 0.357 (0.295) | 0.443 (0.192) | 0.530 (0.241) |
| T 1/2el(hr) | NR | 1.93 | 4.44 (1.22) | 6.17 (4.36) | 5.35 (2.72) | 6.66 |
| Kel (1/hr) | NR | 0.358[b] | 0.164 (0.04) | 0.157 (0.09) | 0.150 (0.06) | 0.104 |

[a]values presented as median (range)
[b]values represent only one subject
NR missing or not reportable data Results after multiple dose dronabinol administration are further illustrated in FIGS. 16-19 and 29.

The results demonstrate that with the exception of Treatment B, the deep-lung inhalation treatments resulted in similar plasma 11-OH-delta-9-THC concentration-time profiles with rapidly reached peak concentrations and equally quick decline in post peak concentrations on both Days 1 and 5. For the five Treatments C, D, E, F, and G, the mean Tmax ranged from 0.115 hours (Treatment F) to 0.208 hours (Treatment C) on Day 1 (mean Cmax range of 0.614 ng/mL for Treatment C to 2.384 ng/mL for Treatment G) and from 0.084 hours (Treatment F) to 0.208 hours (Treatment C) on Day 5 (mean Cmax range of 0.466 ng/mL for Treatment C to 3.476 mg/mL for Treatment F). All subjects in Treatment B had OH-delta-THC concentration values below the 0.500 ng/mL limit of quantification.

compared to those observed following the first doses of the five deep-lung inhalation treatments with concentration values above the Below Quantifiable Limit (BQL) measurement The results show that with the exception of the 2.0 mg deep-lung inhalation dose level tested at the 53, 77, and 101 hour (P=0.01478), 11-OH-delta-9-THC was at steady state for the remaining dose levels at all the timepoints tested (P>0.05 for all treatments).

The results of the dose proportionality assessment for plasma 11-OH-delta-9-THC following deep-lung inhalation of dronabinal are summarized in FIGS. 13-19. Dose normalization was based on the total dronabinol mg dose administered. Treatment B was excluded from both Day 1 and Day 5 comparisons, since all the concentration values for this Treatment were below the limit of quantification. For the remaining Treatments C, D, E, F, and G, following the first (Day 1) dosing, the main effects were not significant for Cmax/Dose and for AUC(0-t)/Dose (P-values of 0.5729 and 0.8939, respectively), but were significant for AUC(0-inf)/Dose (P-value of 0.0016). Following the last dose on Day 5, the main effects were not significant for any of the dose normalized parameters, since with the exception of Cmim/Dose, all the P-values were greater than 0.05. The P-value for Cmim/Dose could not be determined, since all the 11-OH-delta-9-THC Cmin values for all the treatments were below the limit of quantification.

Comparison of the pharmacokinetic parameters of dronabinol and 11-OH-delta-9-THC following a single 5 mg oral dose of dronabinol given in Treatment A with the 6 ascending deep-lung-inhalation doses indicate that the inhalation doses were more rapidly and efficiently absorbed than oral dronabinol with a Tmax range of 0.03-0.5 hours. Equivalent AUC values to 5 mg oral dronabinol were obtained from an inhaled dose between 0.2 and 0.4 mg. In addition, the ratio of the 11-OH metabolite AUC to dronabinol AUC was about five times lower for the inhaled administration route when compared to oral delivery, indicating that oral dronabinol underwent more extensive first-pass metabolism than inhaled dronabinol.

Comparisons of the pharmacokinetic parameters between the first and last multiple deep-lung inhalation dose of each treatment showed no apparent differences in Cmax of dronabinol and 11-OH-delta-9-THC. However, T1/2el increased considerably between Day 1 and Day 5 doses, particularly for Treatments D, E, F, and G. Although for higher dose levels the values of mean AUC(111-135) were higher than the values of AUC(0-inf) for respective treatments, a direct comparison between these two parameters is not appropriate based on the design of this study. The observed increases in half-lives during repeated dosing with dronabinol may indicate insufficient assay sensitivity to detect the true elimination phase of the two analytes, what may lead to substantial accumulation of both the drug and its active metabolite with long term multiple dosing.

Results of dose proportionality assessments for the first and for the last multiple doses of dronabinol and 11-OH-delta-9-THC showed some statistically significant differences; however, there were no apparent patterns in these differences, with the one possible exception of Cmax values increasing less than proportionally for the 2.0 and 2.4 dose levels. Since at higher dose levels the remaining parameters appeared to be relatively dose proportional, assay sensitivity is the more likely cause of these apparent differences, rather than dose dependent kinetics.

Following the 5 mg oral dose given in Treatment A, the mean Cmax was approximately three fold smaller, the AUC values were comparable, and the mean Tmax was 33 times longer compared to the lowest, 0.2 mg, single-dose deep-lung inhalation of dronabinol given in Treatment B. Based on relative AUC(0-inf) vales, the 0.2 mg inhalation dose was about 20-fold more available than the oral dose.

However, the pharmacokinetics of the active metabolite, 11-OH-delta-9-THC, showed the opposite trend. The mean Cmax following Treatment A was higher compared to all the single- and multiple-dose deep-lung inhalation treatments, with the exception of the last multiple-dose administration of Treatment G, where the mean Cmax value was identical to that of Treatment A. Following Treatment B, all 11-OH-delta-9-THC concentrations for both the single and multiple dose treatments were below the BQL. These observations indicate that following oral administration dronabinol undergoes high first pass metabolism, which includes conversion to the 11-OH-delta-9-THC metabolite. Based on these data, oral first pass is about 6-fold more efficient than inhalation first pass.

The results of dose proportionality assessment for the first dose of the 6 deep-lung inhalation treatments indicate that Cmax and AUC(0-t) show evidence of not being dose proportional, whereas AUC(0-inf) is dose proportional. Results for dose normalized Cmax are particularly inconsistent and show no discernable pattern. For example, dose normalized Cmax for Treatment F statistically appears not to be different from dose normalized Cmax values from any other treatment. However, the overall trend in Cmax values seems to indicate that Cmax values increase less than proportionally at the 2.0 and 2.4 mg dose levels. The results of dose normalized AUC (0-t) are somewhat easier to explain, in that only Treatment B appears to be significantly different from the other treatments. The most likely reason is that the observed dronabinol concentrations following the 0.2 mg dose given in Treatment B quickly decrease to below the BQL, and consequently, once dose normalized, the AUC(0-t) for Treatment B appears to be significantly lower than that of the other, higher dose treatments. The apparent dose proportionality of AUC(0-inf) suggests no apparent dose dependent kinetic effects on total drug exposure following single dose administration of dronabinol within the 0.2 mg to 2.4 mg dosing range studied.

The results of dose proportionality assessment for the first doses of the 6 deep-lung inhalation treatments are not consistent with the results observed following the last dose of each multiple-dose regimen. Following multiple dosing the only statistically dose proportional parameter for dronabinol appears to be Cmax. However, even for Cmax, the mean values increase less than proportionally at the 2.0 and 2.4 mg dose levels, similarly to what was observed following the first dose of each treatment. While Cmin appears not to be dose proportional, this is due to dronabinol concentrations for Treatments B, C, D, and E declining to below the limit of quantification during the sampling interval; whereas for Treatments F and G they remained above the BQL. Since dose normalized Cmin values are similar for Treatments F and G, it is likely that Cmin is actually dose proportional, but that the current assay is not sensitive enough to detect dose proportionality for Cmin at all dose levels tested.

The issue of assay sensitivity becomes also a factor in evaluating the results of dose proportionality assessment for AUC(111-135) and Cavg, since we have defined Cavg as AUC(111-135)/24. It appears that Treatments B and C have a substantially lower dose normalized AUC(111-135) compared to Treatments D, E, F, and G. Generally, in case of dose-dependent kinetics, the opposite pattern would be expected. Evaluation of the concentration data collected for each subject during the Hour 111-135 sampling interval shows that no detectable dronabinol concentrations have been reported in any of the subjects beyond the Hour 113 sample for Treatment B and beyond the Hour 115 sample for Treatment C. For Treatments D and E, some subjects have detectable levels up to 123 hr, whereas for Treatments F and G, values remained above BQL throughout the sampling interval. Consequently, while based on these results the assessment of dose proportionality for dronabinol AUC(111-135), Cmin, and Cavg at all dose levels cannot be made, evidence from the higher dose levels suggests that no dose dependency exists for any of these parameters.

Results of dose proportionality assessment for 11-OH-delta-9-THC pharmacokinetic parameters following multiple-dose deep-lung inhalation treatments with dronabinol show that all the parameters were essentially dose proportional. However, the Cmax values also appeared to increase less/than proportionally at the 2.0 and 2.4 mg dose levels; a trend similar to what was observed for the parent compound. Treatment B was excluded from all comparisons due to all concentration values being below the BQL. For the remaining five treatments, the main effects were not statistically significant (P<0.05) for any of the 11-OH-delta-9-THC parameters following the last dose, and for Cmax and AUC(0-t) following the first dose of the deep-lung inhalation treatments. Although following the first dronabinol dose, the 11-OH-delta-9-THC dose normalized AUC(0-inf) for Treatment C was substantially lower than for Treatments D, E, F, and G, as mentioned earlier in this discussion, only 3 subjects in Treatment C had calculable AUC(0-inf). Since the extrapolated portion of their AUC(0-inf) varied from 95% for Subject 21 to 44% for Subject 17, AUC(0-inf) estimates cannot be considered accurate for this treatment. AUC(0-inf) was dose proportional for Treatments D, E, F, and G.

The design of the multiple dose portion of the study, where each of the 6 deep-lung inhalation dose levels was administered every 5 hours for 4 daytime doses, followed by a 9 hour nighttime interval prior to the next (morning) dose, with the pattern repeating until 12 consecutive doses were given, precludes a direct comparison between the AUC values on Day 1 and Day 5. The inconsistent intervals between doses results in both the drug and its metabolites not being at steady state during the sampling interval. Consequently, the comparison between steady state AUC(0-0), where 0 is the dosing interval, and single dose AUC(0-inf) cannot be made. Generally, for a drug which dose not alter its own kinetics with multiple dosing, the two AUC values can be expected to be the same.

Based on the Cmin values of 0 for both the drug (Treatments B through E) and 11-OH-delta-9-THC (all treatments), it can be concluded that little accumulation of either compound is taking place. In that case, a direct comparison between AUC(0-inf) values between the single and last multiple dose could be made for each treatment. However, due to questions of accuracy of extrapolation for AUC(0-inf), this comparison would be of limited value for the current data. Furthermore, since due to assay sensitivity it is possible that the observed terminal phase is the distribution and not the elimination phase, comparison of AUC(0-24) (single dose) with AUC(111-135) for multiple dose is also inappropriate. The disproportionate increases in AUC(111-135) compared to AUC(0-24) for a given treatment are more likely an indication of accumulation of the drug and metabolite in the plasma, as opposed to changes in pharmacokinetics of the two compounds with multiple dosing.

The reasons for suspecting that the observed half-lives are representative of distribution rather than elimination phase are twofold. First, while the observed half-lives for single doses of dronabinol are relatively similar for the 6 inhalation dose levels, for the multiple doses for Treatment D and higher they begin to increase disproportionately. For example, for Treatment G, the mean half-lives are 1.69 h for Day 1 and 20.6 h for Day 5. This suggests that at lower dose levels even following multiple dose administrations the true elimination phase may have been either completely missed or at least underestimated. Furthermore, at lower dose levels, the Kel intervals were also assigned over shorter time intervals due to concentrations decreasing to below quantifiable levels faster.

The second reason is that while similar trends can be observed for the 11-OH-delta-9-THC data, the increases in the half-lives following multiple dosing are not as dramatic as those observed for dronabinol. As a consequence, for Treatment G, for example, the mean half-lives are 2.04 h for Day 1 and 6.66 h for Day 5. Therefore, on Day 5, the half-life of the metabolite is significantly shorter than that of the parent compound—a situation which is kinetically impossible, and which suggests that even at highest dose level of dronabinol the observed terminal phase is still not the true elimination phase for the metabolite.

Evaluation of the effects of dronabinol and 11-OH-delta-9-THC on the chosen pharmacodynamic markers, pulse rate and conjunctiva congestion, have not shown any dose-related effects or any apparent variability between the subjects receiving placebo and those receiving dronabinol. For pulse rate, the actual evaluations for the first/single dronabinol dose were based on a predose and four additional postdose observations taken at Hours 0.83, 1.83, 3.83, and 47.25. Within the last (Hours 111-135) dosing period, pulse rate was evaluated only 3 times. Consequently, only maximum and minimum rates and the fluctuation index could be reported from these data. For conjunctiva congestion, only predose and Hour 5 assessments were made following Day 1 dosing, while the last assessment was made at Hour 111. No parameters could be determined from these data.

C. Pharmacodynamics and Safety

Values of pulse rate and conjunctiva congestion assessment scale were listed and summarized using descriptive statistics. Although compartmental and non-compartmental modeling was planned for the pharmacodynamic (PD) markers, insufficient data were collected for either type of modeling. No parameters could be calculated from the conjunctiva congestion scale due to insufficient number of observations. For pulse rate, the parameters were calculated from the pulse rate data collected following the single oral dose and first and last doses of multiple deep-lung inhalations of dronabinol.

Max Maximum observed pulse rate during the sampling interval.

Min Minimum observed pulse rate during the sampling interval.

Tmax Time of the observed maximum pulse rate (obtained without interpolation).

Tmin Time of the observed minimum pulse rate (obtained without interpolation).

FI Fluctuation index, calculated as: (Max-Min)×100/Min

Based on the protocol, changes in pulse rate and conjunctiva congestion were evaluated with respect to dronabinol and 11-OH-delta-9-THC blood levels. However, since the majority of pulse rate measurements and conjunctiva congestion assessments were taken on Days 3 and 4, and on Day 5 prior to the 111-hour timepoint, which signified the start of the actual dosing period of pharmacokinetic interest, only a general evaluation of the entire mean and individual pulse rate and conjunctiva congestion assessment profiles for each dosing period was possible.

Descriptive statistics were reported for vital sign measurements (pulse, sitting systolic and diastolic blood pressure, and respiration rate) by time of collection and change from predose for each treatment group. The last observation obtained prior to dosing (including rechecks) was used as the predose measurement. No postdose rechecks were used in summarization of vital signs.

Descriptive statistics were reported for changes from predose in conjunctiva congestion. The following cognitive assessments were listed by subject and summarized by timepoint of collection: Continuous Performance Test, Digital Symbol Substitution Test, Hand-Eye Coordination Test, Randt Picture Recognition Test, and Sedation Observation Rating.

Descriptive statistics were reported for changes from predose in pulmonary function test. The following pulmonary function test assessments were listed by subject: FVC (Forced Vital Capacity (L)), FEV (Forced Expiratory Volume in one (1) Second (L)), FEV1/FVC, $FEF_{25-75\%}$, and PFER.

1. Pulse Rate

Dose-related effects of dronabinol and 11-OH-delta-9-THC on pulse rate were assessed by reporting each subject's pulse rate values, in beats per minute (bpm), following the single and multiple dose administrations of dronabinol. The arithmetic means of parameters calculated from pulse rate values following single dose dronabinol administration for Treatments A through G are summarized in the Table 8.

following the first/single dronabinol dose, an insufficient number of pulse rate assessments were collected to accurately estimate AUC(0-t).

2. Conjunctiva Congestion

Dose-related effects of dronabinol and 11-OH-delta-9-THC on conjunctiva congestion were assessed by reporting each subject's conjunctiva congestion scores following the single and multiple dose administrations of dronabinol. Conjunctiva congestion was not assessed for subjects in Treatment A.

TABLE 8

Mean (SD) Pulse Rate Values Following Single Dose Dronabinol Administration (Day 1)

| Parameters | Oral Dose 5 mg (Treatment A) | Nebulized Dose | | | | | |
|---|---|---|---|---|---|---|---|
| | | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| Max (bpm) | 75 (11) | 78 (9) | 80 (18) | 79 (12) | 81 (10) | 82 (22) | 88 (15) |
| Min (bpm) | 62 (6) | 61 (9) | 56 (7) | 60 (10) | 64 (6) | 59 (3) | 61 (7) |
| Tmax (hr) | 8.60 (18.9) | 24.1 (26.0) | 24.7 (25.4) | 40.0 (19.2) | 1.50 (1.21) | 0.830 (0.00) | 10.2 (20.9) |
| Tmin (hr) | 10.1 (18.3) | 2.22 (1.89) | 2.22 (1.89) | 2.19 (1.45) | 9.19 (18.9) | 9.87 (21.1) | 2.06 (1.74) |
| FI[a] | 20.5 (7.48) | 30.2 (11.3) | 44.3 (32.8) | 32.2 (9.43) | 27.3 (7.26) | 37.3 (31.6) | 44.9 (21.3) |

[a]Fluctuation Index, calculated as: (Cmax − Cmin) × 100/Cmin

Figure 20:
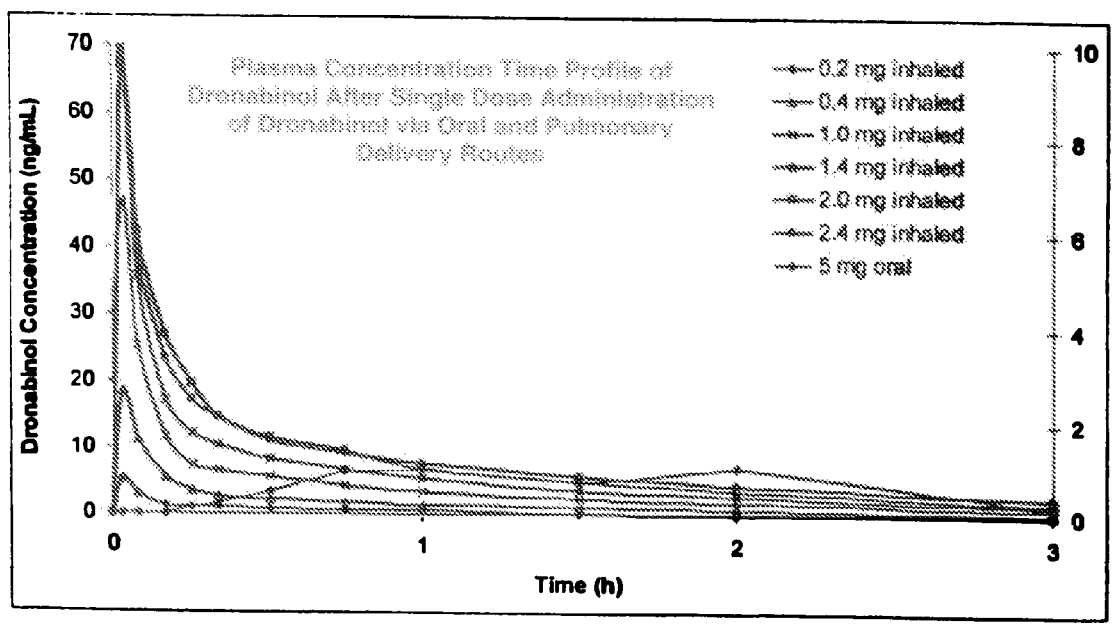
FIG. 20 is a graph showing the plasma concentration-time profile of dronabinol after single dose administration of dronabinol via oral and pulmonary delivery routes (0-3 hours).
Figure 21:
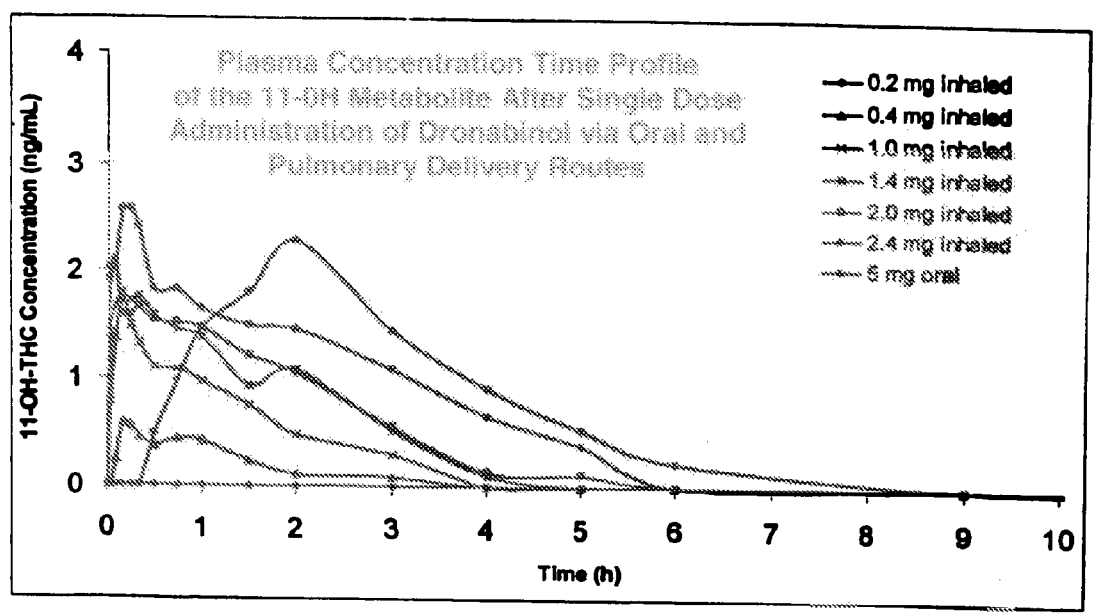
FIG. 21 is a graph showing the plasma concentration-time profile of the 11-OH metabolite after single dose administration of dronabinol via oral and pulmonary delivery routes (0-10 hours).
Figure 22:
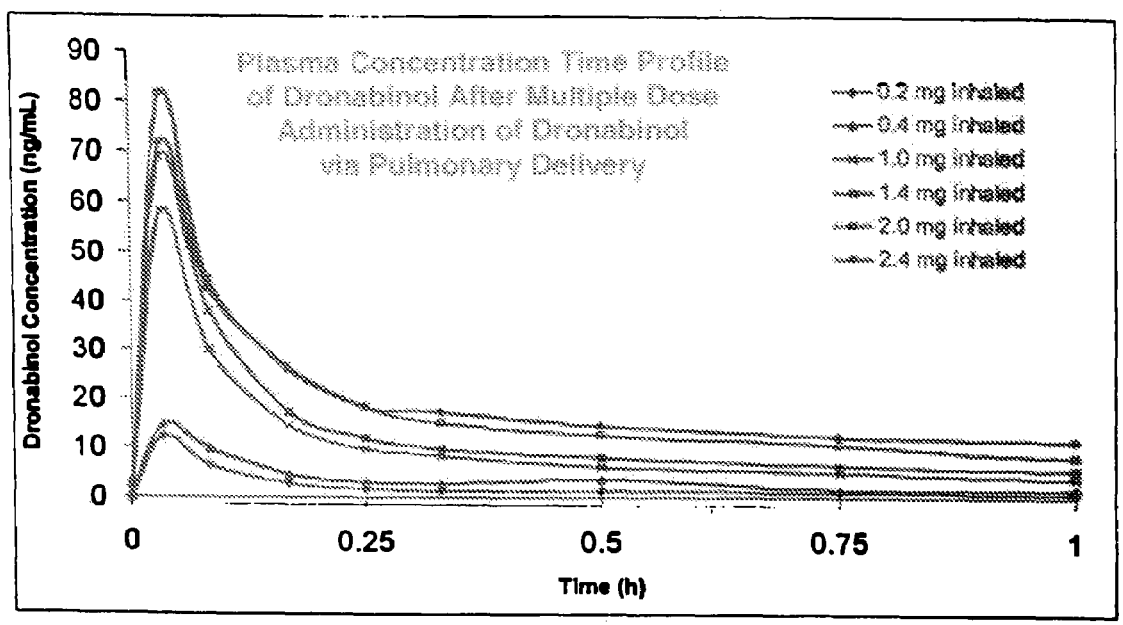
FIG. 22 is a graph showing the plasma concentration-time profile of dronabinol after multiple dose administration of dronabinol via pulmonary delivery (0-1 hour).

The mean pulse rate versus time curves for these treatments are presented in FIG. 20.

The results show that there was substantial variability in the pulse rates of all subjects in this study, however, no discernable pattern of change in pulse rates was apparent for any of the dose levels or for the comparison of first versus last dosing interval data.

The mean pulse rate parameters following the dronabinol dose on Day 5 of each of the 6 deep-lung inhalation treatments are presented in Table 9.

Figure 23:
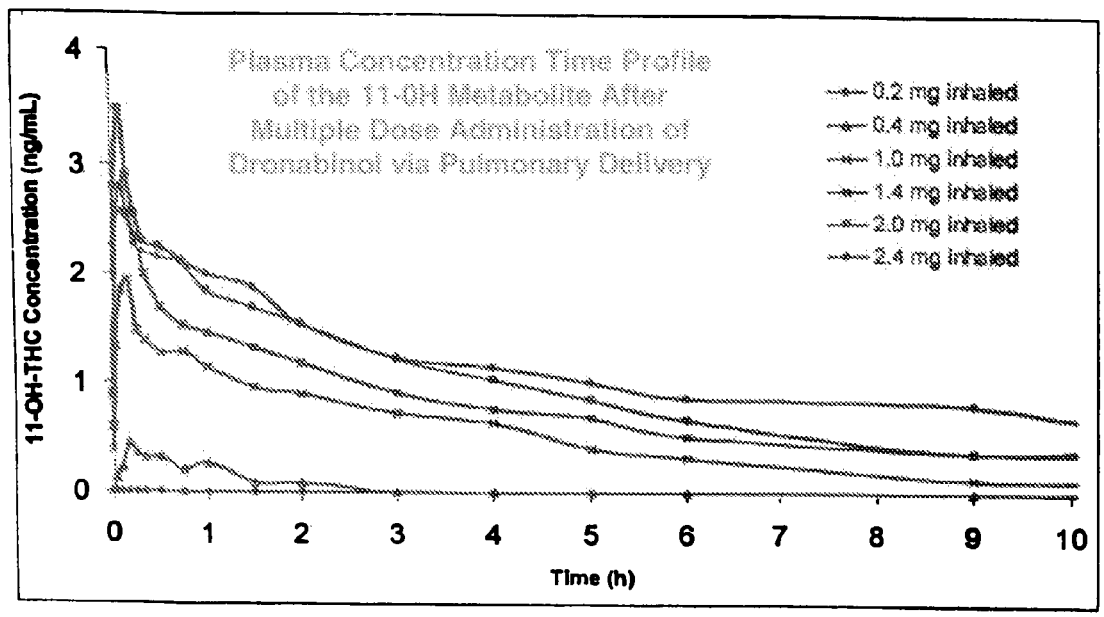
FIG. 23 is a graph showing the plasma concentration-time profile of the 11-OH metabolite after multiple dose administration of dronabinol via pulmonary delivery (0-10 hours).

The mean conjunctiva congestion scores versus time curves for these treatments are presented in FIG. 23 (linear scale, with S.D.), FIG. 24 (linear scale, without S.D.), and FIG. 25 (semi-log scale). The figures show that there was substantial variability in the conjunctiva congestion scores of all subjects in this study; however, no discernable pattern was apparent in the changes for any of the dose levels or for the comparison of first versus last dosing interval data.

No parameters could be evaluated from the conjunctiva congestion scale assessment, due to insufficient number of

TABLE 9

Mean (SD) Pulse Rate Values Following Multiple Dose Dronabinol Administration (Day 5)

| Parameters | Nebulized Dose | | | | | |
|---|---|---|---|---|---|---|
| | 0.2 mg (Treatment B) | 0.4 mg (Treatment C) | 1.0 mg (Treatment D) | 1.4 mg (Treatment E) | 2.0 mg (Treatment F) | 2.4 mg (Treatment G) |
| Max(bpm) | 78 (15) | 75 (10) | 88 (24) | 86 (12) | 92 (14) | 80 (7) |
| Min(bpm) | 67 (11) | 62 (11) | 68 (12) | 71 (5) | 69 (9) | 62 (9) |
| Tmax(hr) | 2.06 (1.55) | 0.777 (1.53) | 1.28 (1.98) | 1.60 (1.88) | 0.766 (1.71) | 0 |
| Tmin(hr) | 1.92 (1.71) | 1.92 (1.21) | 2.38 (1.20) | 2.06 (0.972) | 2.30 (0.854) | 1.92 (0.00) |
| FI[a] | 17.2 (8.59) | 21.3 (13.4) | 28.1 (22.6) | 21.2 (14.7) | 33.6 (17.7) | 30.6 (15.9) |

[a]Fluctuation Index, calculated as: (Cmax − Cmin) × 100/Cmin

Since in addition to predose, only three pulse rate measurements were taken following the last deep-lung inhalation dose of each treatment, and since the last measurement was collected at 114.83 hours, no estimates of AUC(111-135) have been included for the pulse rate parameter tables. Similarly, assessments performed following both first and last dronabinol dose. Following the first dose, and through the subsequent 48-hour pharmacokinetic sampling period, only two assessments were taken, one at predose (Hour 0) and one at Hour 5. Since the last conjunctive congestion assessment for all subjects in Treatments B through G was taken at Hour 111, essentially no conjunctiva congestion data was collected in the last dosing period of interest (Hours 111 through 135).

The majority of pulse rate measurements and conjunctiva congestion assessments were taken on Days 3 and 4, and on Day 5 prior to the Hour 111 timepoint which signified the start of the actual dosing period of pharmacokinetic interest. This scheduling of pharmacodynamic assessments presented a problem in fulfilling the protocol requirements for comparison between pharmacodynamic markers and blood levels of dronabinol and 11-OH-delta-9-THC since no blood levels were collected on those days. Consequently, only a general evaluation of the mean and individual pulse rate and conjunctiva congestion profiles for each dosing period could be performed. These showed no apparent differences in pulse rates or conjunctiva congestion levels between the single oral, and the single and multiple deep-lung inhalations of dronabinol. In addition, within each treatment group, there were no apparent differences between pharmacodynamic parameters of individuals receiving placebo and those receiving the actual dronabinol dose.

D. Conclusion

In conclusion, comparison of the pharmacokinetic parameters of dronabinol and 11-OH-delta-9-THC following a single 5 mg oral dose of dronabinol given in Treatment A with the 6 ascending deep-lung-inhalation doses indicate that the inhalation doses were more rapidly and efficiently absorbed. In addition, the greater dronabinol/11-OH-delta-9-THC ratios indicate that oral dronabinol underwent more extensive first-pass metabolism than inhaled dronabinol.

Further, comparisons of the pharmacokinetic parameters between the first and last multiple deep-lung inhalation dose of each treatment showed no apparent differences in Cmax of dronabinol and 11-OH-delta-9-THC. However, T1/2el increased considerably between Day 1 and Day 5 doses, particularly for Treatments D, E, F, and G. Although for higher dose levels the values of mean AUC(111-135) were higher than the values of AUC(0-inf) for respective treatments, a direct comparison between these two parameters is not appropriate based on the design of this study. The observed increases in half-lives during repeated dosing with dronabinol may indicate insufficient assay sensitivity to detect the true elimination phase of the two analytes, what may lead to substantial accumulation of both the drug and its active metabolite with long term multiple dosing.

Neither single nor multiple dose administrations of dronabinol had any apparent effect on pulse rate or conjunctiva congestion, and no apparent differences were discernable in these assessments between subjects receiving placebo and those receiving the active dronabinol treatments.

Dronabinol appeared to be generally well-tolerated up to the highest inhaled dose (2.4 mg). "Cough during dosing" was the most common AE reported during the trial. This cough was experienced by the majority of the subjects following the inhalation treatments, both active and placebo.

No treatment-related differences were observed regarding any physical examination, vital sign measurement, ECG, clinical laboratory result, pulmonary function measurement, or psychomotor performance test. Psychomotor performance evaluations demonstrated a reduction in sustained attention and motor reaction time, better coordination, a slowing of memory retrieval and reduction in executive function and speed of processing.

The above-mentioned patent and publications are incorporated herein by reference. While there is described above the principles of this invention in connection with a specific drug and specific semiaqueous solvents, it is to be clearly understood that this description is made only by way of example, and not as a limitation to the scope of this invention. For example, as a raw drug, synthetic or natural source-derived delta-9-tetrahydrocannabinol can be used, as well as prodrugs, isomers, derivatives, metabolites, and the like. Generally a wide variety of hydroxy containing solvents can be used, such as isopropanol instead of ethanol and polypropylene glycol instead of propylene glycol, so long as they are pharmaceutically-acceptable. All such variations are within the full intended scope of the appended claims. The contents of all cited references throughout this application are hereby expressly incorporated by reference. The practice of the present invention will employ, unless otherwise indicated, conventional techniques of pharmacology and pharmaceutics, which are within the skill of the art.

What is claimed is:

1. A stable composition for rapid delivery by inhalation to the lungs, and subsequently to the bloodstream, the composition comprising a therapeutically effective amount of delta-9-tetrahydrocannabinol in a pharmaceutically-acceptable semiaqueous solvent consisting essentially of an alcohol, water and a glycol, in amounts sufficient
    (i) to aerosolize the composition to a mean mass median aerodynamic diameter in the range of from about 1 up to about 10 μM;
    (ii) to enhance partitioning by producing a stable clear solution near the solubility point of the delta-9-tetrahydrocannabinol;

(iii) wherein the concentration of glycol is about 20% to about 65% of the solvent; and (iv) wherein the concentration of the alcohol is 20% to about 70% of the solvent.

2. The composition of claim 1 wherein said delta-9-tetrahydrocannabinol comprises from about 0.1 to about 200 mg/mL.

3. The composition of claim 2 wherein said delta-9-tetrahydrocannabinol comprises from 0.1 to 25 mg/mL.

4. The composition of claim 2 wherein said delta-9-tetrahydrocannabinol comprises 50 mg/mL.

5. The composition of claim 1 wherein said solvent comprises ethanol, water and propylene glycol.

6. The solvent of claim 1 wherein the volumetric ratios of the alcohol:water:glycol are selected from those in the range of from 20 to about 70:about 10 to about 30:about 20 to about 65, respectively, having a combined total of 100.

7. The solvent of claim 5 wherein the volumetric ratios of ethanol:water:propylene glycol are selected from those in the range of from 20-70:10:20-65, respectively, having a combined total of 100.

8. The solvent of claim 7 wherein the volumetric ratios of ethanol:water:propylene glycol are 35:10:55, respectively, having a combined total of 100.

9. The composition claim 1 wherein the composition is in a sterile and/or preserved sealed unit-or-multi-unit dosage form comprising a container for rapid delivery by inhalation to the lungs and subsequently to the bloodstream.

10. The composition claim 9 wherein said container comprises Type I Amber Glass with a liner.

* * * * *

UNITED STATES PATENT AND TRADEMARK OFFICE
CERTIFICATE OF CORRECTION

PATENT NO. : 7,648,696 B2                                                                         Page 1 of 1
APPLICATION NO. : 10/656304
DATED : January 19, 2010
INVENTOR(S) : McPhillips et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 636 days.

Signed and Sealed this

Twenty-third Day of November, 2010

David J. Kappos
*Director of the United States Patent and Trademark Office*